(12) United States Patent
Raines et al.

(10) Patent No.: US 9,371,521 B2
(45) Date of Patent: Jun. 21, 2016

(54) SUBSTITUTED PYRAZINEDITHIOL REDUCING AGENTS

(71) Applicant: Wisconsin Alumni Research Foundation, Madison, WI (US)

(72) Inventors: Ronald Thaddeus Raines, Madison, WI (US); John C. Lukesh, III, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 14/319,972

(22) Filed: Jun. 30, 2014

(65) Prior Publication Data

US 2015/0376591 A1 Dec. 31, 2015

(51) Int. Cl.
| | |
|---|---|
| *C07D 241/10* | (2006.01) |
| *C07D 241/38* | (2006.01) |
| *C12N 9/50* | (2006.01) |
| *C07D 495/04* | (2006.01) |
| *C07D 241/12* | (2006.01) |
| *C12N 9/12* | (2006.01) |

(52) U.S. Cl.
CPC ................ *C12N 9/63* (2013.01); *C07D 241/12* (2013.01); *C07D 495/04* (2013.01); *C12N 9/1223* (2013.01); *C12Y 207/03002* (2013.01); *C12Y 304/22002* (2013.01)

(58) Field of Classification Search
CPC ........................... C07D 241/10; C07D 241/38
USPC .................................................. 544/336, 350
See application file for complete search history.

(56) References Cited

U.S. PATENT DOCUMENTS

| | | | |
|---|---|---|---|
| 4,659,733 A | 4/1987 | DuPriest et al. | |
| 4,755,528 A | 7/1988 | DuPriest et al. | |
| 5,651,960 A | 7/1997 | Chan et al. | |
| 5,910,435 A | 6/1999 | Raines et al. | |
| 6,436,973 B1 | 8/2002 | Danvy et al. | |
| 6,972,320 B2 | 12/2005 | Raines et al. | |
| 7,256,259 B2 | 8/2007 | Raines et al. | |
| 7,317,129 B2 | 1/2008 | Raines et al. | |
| 2005/0002886 A1 | 1/2005 | Philippe et al. | |
| 2010/0048866 A1 | 2/2010 | Raines et al. | |
| 2013/0211055 A1 | 8/2013 | Raines et al. | |

OTHER PUBLICATIONS

Bednar (1990) "Reactivity and pH dependence of thiol conjugation to N-ethylmaleimide: detection of a conformational change in chalcone isomerase," *Biochemistry*. 29:3684-3690.
Benesch et al. (1955) "The Acid Strength of the -SH Group in Cysteine and Related Compounds," *J. Am. Chem. Soc.* 77:5877-5881.
Burns et al. (1990) "Predicting the stability of cyclic disulfides by molecular modeling: effective concentrations in thiol-disulfide interchange and the design of strongly reducing dithiols," *J. Am. Chem. Soc.* 112:6296-6303.
Cleland (1964) "Dithiothreitol, a New Protective Reagent for SH Groups," *Biochemistry*. 3:480-482.
Cumming et al. (2004) "Protein Disulfide Bond Formation in the Cytoplasm during Oxidative Stress," *J. Biol. Chem.* 279:21749-21758.
Evans et al. (1949) "Dithiols. Part III. Derivatives of polyhydric alcohols," J. Chem. Soc. 248-255.
Fernandes et al. (2004) "Theoretical Insights into the Mechanism for Thiol/Disulfide Exchange," *Chem. Eur. J.* 10:257-266.
Gilbert (1990) "Molecular and cellular aspects of thiol-disulfide exchange," *Adv. Enzymol.* 63:69-172.
Houk et al. (1987) "Structure-reactivity relations for thiol-disulfide interchange," *J. Am. Chem. Soc.* 109:6825-6836.
Keire et al. (1992) "Kinetics and equilibria of thiol/disulfide interchange reactions of selected biological thiols and related molecules with oxidized glutathione," *J. Org. Chem.* 57:123-127.
Kessler et al. (Sep. 26, 1994) "Design and synthesis of a novel site-directed reducing agent for the disulfide bond involved in the acetylcholine binding site of the AChoR," Tetrahedron Letters. 35(39):7237-7240.
Keyworth (1959) "Notes: Ionization Constants for Some Piperazine Derivatives," *J. Am. Chem. Soc.* 24:1355-1356.
Lamoureux et al. (1993) "Synthesis of dithiols as reducing agents for disulfides in neutral aqueous solution and comparison of reduction potentials," *J. Org. Chem.* 58:633-641.
Lees et al. (1991) "Meso-2,5-Dimercapto-N,N,N',N'-tetramethyladipamide: a readily available, kinetically rapid reagent for the reduction of disulfides in aqueous solution," *J. Org. Chem.* 56:7328-7331.

(Continued)

Primary Examiner — Douglas M Willis
(74) Attorney, Agent, or Firm — Lathrop & Gage LLP

(57) ABSTRACT

Substituted dithiol pyrazine compounds useful as reducing agents in biologically relevant media having formula:

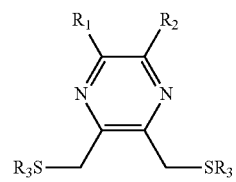

where variables are defined herein and corresponding oxidized pyrazine dithianes. Reducing agents useful to reduce disulfide bonds, particularly in proteins, or to prevent the formation of disulfide bonds, particularly in proteins, and other biological molecules. Reducing agents useful to regulate protein function in proteins in which a sulfhydryl group is associated with biological activity. Reducing agents useful and suitable for application in a variety of biological applications, particularly as research and synthetic reagents. S-acylated dithiol pyrazine compounds, where $R_3$ is an acyl group, are selectively activated as reducing agents by removal of the S-acyl groups enzymatically or chemically. Dithiol pyrazine reducing agents and corresponding S-acylated dithiol pyrazines, immobilized on surfaces or conjugated to other chemical species, are provided.

21 Claims, 6 Drawing Sheets

(56) References Cited

OTHER PUBLICATIONS

Lees et al. (1993) "Equilibrium constants for thiol-disulfide interchange reactions: a coherent, corrected set," *J. Org. Chem.* 58:642-647.

Liu et al. (2000) "The Syntheses of Pyrazino-Containing Sultines and Their Application in Diels—Alder Reactions with Electron-Poor Olefins and [60]Fullerene," *J. Org. Chem.* 65:3395-3403.

Lukesh et al. (Feb. 21, 2012) "A Potent, Versatile Disulfide-Reducing Agent from Aspartic Acid," *J. Am. Chem. Soc.* 134:4057-4059.

Lukesh et al. (Jul. 11, 2014) "Pyrazine-Derived Disulfide-Reducing Agent for Chemical Biology," *Chem Commun.* 50:9591-9594.

Lukesh et al. (Oct. 10, 2013) "Thiols and Selenols as Electron-Relay Catalysts for Disulfide-Bond Reduction," *Angew. Chem. Int. Ed.* 52:12901-12904.

Millis et al. (1993) "Oxidation/reduction potential of glutathione," *J. Org. Chem.* 58:4144-4146.

Oetke et al. (2002) "Versatile Biosynthetic Engineering of Sialic Acid in Living Cells Using Synthetic Sialic Acid Analogues," *J. Biol. Chem.* 277:6688-6695.

Patel et al. (Jan. 15, 2012) "Oxidative folding of lysozyme with aromatic dithiols, and aliphatic and aromatic monothiols," Bioorg. Med. Chem., 2012, 20, 1020-1028.

Ranganathan et al. (1991) "Highly efficient propane-1,3-dithiol mediated thiol—disulphide interchange: A facile and clean methodology for S—S reduction in peptides," Chem. Commun. 934-936.

Rothwarf et al. (1992) "Equilibrium and Kinetic Constants for the Thiol-Disulfide Interchange Reaction Between Glutathione and Dithiothreitol," *Proc. Natl. Acad. Sci. U.S.A.* 89:7944-7948.

Servent et al. (Mar. 6, 1995) "Site-directed disulfide reduction using an affinity reagent: Application on the nicotinic acetylcholine receptor," FEBS Letters. 360:261-265.

Shaked et al. (1980) "Rates of thiol-disulfide interchange reactions involving proteins and kinetic measurements of thiol pKa values," *Biochemistry.* 19:4156-4166.

Singh et al. (1991) "A reagent for reduction of disulfide bonds in proteins that reduces disulfide bonds faster than does dithiothreitol," *J. Org. Chem.* 56:2332-2337.

Singh et al. (Mar. 1994) "Reagents for Rapid Reduction of Native Disulfide Bonds in Proteins," Bioorg. Chem. 22:109-115.

Singh et al. (1995) "Reagents for rapid reduction of disulfide bonds," Methods Enzymol. 251:167-173.

Smith et al. (1975) "Simple alkanethiol groups for temporary blocking of sulfhydryl groups of enzymes," *Biochemistry.* 14:766-771.

Szajewski et al. (1980) "Rate constants and equilibrium constants for thiol-disulfide interchange reactions involving oxidized glutathione," *J. Am. Chem. Soc.* 102:2011-2026.

Van Laer et al. (Oct. 17, 2012) "Low-Molecular-Weight Thiols in Thiol-Disulfide Exchange," *Antioxid. Redox Signal.* 18:1642-1653.

Whitesides et al. (1977) "Rates of thiol-disulfide interchange reactions between mono- and dithiols and Ellman's reagent," *J. Org. Chem.* 42:332-338.

Woycechowsky et al. (1999) "A small-molecule catalyst of protein folding in vitro and in vivo," *Chem. Biol.* 6:871-879.

SUBSTITUTED PYRAZINEDITHIOL REDUCING AGENTS

STATEMENT REGARDING GOVERNMENT FUNDING

This invention was made with government support under GM044783 awarded by the National Institutes of Health. The government has certain rights in the invention.

BACKGROUND OF THE INVENTION

The redox state of cysteine residues can have a profound effect on protein structure and function [1-4]. Consequently, reagents that reduce disulfide bonds to thiols can be crucial to progress in chemical biology [1, 5-6]. The reduction of disulfide bonds within biomolecules is preferably accomplished under mild conditions: in water, at neutral pH, and at room temperature [1, 7-10]. Thiols can accomplish these goals and do so (unlike phosphines) in a reversible manner. The mechanism for reduction involves thiol-disulfide interchange initiated by the attack of a thiolate [11-18]. The use of monothiols such as L-glutathione or β mercaptoethanol (βME) can lead to the trapping of the resulting intermediate as a mixed disulfide. Cleland reported that dithiothreitol (DTT or Cleland's reagent, Table 1), a racemic dithiol, readily completes the reduction reaction by forming a stable six-membered ring [7]. The potency of DTT is evident from the low reduction potential ($E^\circ = -0.327$ V) of its oxidized form [19]. As a result, DTT has achieved widespread use for the quantitative reduction of disulfide bonds in proteins and other biomolecules.

DTT has, however, a serious limitation. Because thiolates, but not thiols, are nucleophilic in aqueous solution [20], the observed rate of disulfide reduction is dependent on the thiol pKa of the reducing agent. With thiol pKa values of 9.2 and 10.1, less than 1% of DTT resides are in the reactive thiolate form at neutral pH.8. As a result, several attempts have been made to create water-soluble reducing agents that exhibit depressed thiol pKa values [9, 21-22].

Recently, dithiobutylamine (DTBA, Table 1), a dithiol reducing agent derived from L-aspartic acid was described as a potent disulfide-reducing agent [23]. Moreover, the amino group of DTBA confers depressed thiol pKa values of 8.2 and 9.3 and facile functionalization [23-24]. That amino group, however, appeared to deter the ability of the molecule to reduce certain disulfide bonds due to unfavorable Coulombic interactions [23].

SUMMARY OF THE INVENTION

The present invention provides improved dithiol reducing agents useful, in particular, for the reduction of disulfide bonds. The reducing agents of this invention are pyrazine dithiols and are useful, for example, to reduce disulfide bonds, particularly in proteins, or to prevent the formation of disulfide bonds, particularly in proteins and other biological molecules (e.g., thiolated species, such as thiolated nucleic acids). Reducing agents of this invention can be employed to regulate protein function in proteins in which a sulfhydryl group (such as those of cysteine residues) is associated with biological activity. Reducing agents of this invention can prevent inactivation of a given protein or enhance activation of a given protein or other biological molecule in vitro and/or in vivo. Reducing agents of this invention can prevent or reduce oxidation of cysteine residues in proteins and prevent the formation of reduced activity protein dimers (or other oligomers). Reducing agents of this invention are useful and suitable for application in a variety of biological applications, particularly as research and synthetic reagents.

The present invention provides improved dithiol reducing agents useful, in particular, for the reduction of disulfide bonds. In specific embodiments, the invention provides S-acylated dithiols which can be selectively activated as reducing agents by removal of the S-acyl groups enzymatically or chemically. In specific embodiments, the invention provides dithiol reducing agents and S-acylated dithiols which are immobilized on surfaces, including among others, glass, quartz, microparticles and nanoparticles.

In specific embodiments, pyrazine dithiol reducing agents of this invention exhibit a thiol $pK_a$ value less than 9.0, preferably less than 8.5 and more preferably less than 8.0. In specific embodiments, pyrazine dithiol reducing agents of this invention exhibit disulfide reduction potential more negative than −0.28 V, preferably more negative than −0.30 V and more preferably more negative than −0.32 V.

The invention provides compounds of formula I:

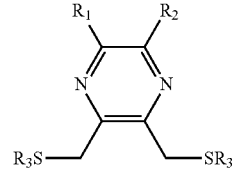

and salts thereof, wherein:

$R_1$ and $R_2$, independently, are hydrogen, halogen, —CN, optionally-substituted alkyl, -alkoxylalkyl, —CO—$R_6$, —CO—O$R_6$, —O—CO—$R_6$, —CO—$R_6$, —CO—CH$_2$—CO—O—$R_6$, —NH—CO—$R_6$, —CO—N($R_6$)$_2$, —NH—CO—N($R_6$)$_2$, a divalent linker carrying a reactive group for immobilization on a solid or for conjugation to a chemical species, a divalent linker immobilized to a solid, or a divalent linker conjugated to a chemical species, where each $R_6$ independently is hydrogen, an alkyl group having 1-6 (preferably 1-3) carbon atoms or an alkoxyalkyl group;

$R_3$ is independently hydrogen or an acyl group (—CO$R_7$), each $R_7$ is independently hydrogen, an alkyl group, an alkoxyalkyl group, an aryl group, a heterocyclic group, or a heteroaryl group, wherein each alkyl, alkoxyalkyl, aryl, heterocyclic or heteroaryl group is optionally substituted with one or more non-hydrogen substituents.

Optional substitution is optional substitution with one or more —OH, oxo moieties (═O, e.g., to form a —CO—), halogen, —CN, —N$_3$, —NO$_2$, —OCN, —NCO, —SCN, —NCS, alkyl, haloalkyl, alkoxy, alkoxyalkyl, haloalkoxy, —NH$_2$, —CO—O$R_8$, —O—CO—$R_8$, —CO—$R_8$, —CO—CH$_2$—CO$_2$—$R_8$, —NH—CO—$R_8$, —CO—N($R_8$)$_2$, —N($R_8$)$_2$, —NH—CO—N($R_8$)$_2$, where each $R_8$ independently is hydrogen, an alkyl group having 1-6 (preferably 1-3) carbon atoms or an alkoxyalkyl group. In an embodiment substituents are one or more halogen, —CN, —N$_3$, —NO$_2$, —OCN, —NCO, —SCN, or —NCS. In an embodiment, substituents are alkyl, haloalkyl, alkoxy, alkoxyalkyl, or haloalkoxy. In an embodiment, substituents are —NH$_2$, —NH—CO—$R_8$, —CO—N($R_8$)$_2$, —N($R_8$)$_2$, —NH—CO—N($R_8$)$_2$. In an embodiment, substituents are —CO—O$R_8$, —O—CO—$R_8$, —CO—$R_8$, or —CO—CH$_2$—CO$_2$—$R_8$. In a more specific embodiment, substituents are alkyl groups having 1-3 carbon atoms, alkoxy groups having 1-3 carbon atoms, —CH$_3$, —C$_2$H$_5$, —CF$_3$, —COH, —COCH$_3$, —F, —Cl, —OCH$_3$, and —OC$_2$H$_5$.

Compounds of formula I are useful as pyrazine dithiol reducing agents and/or as synthetic intermediates for the preparation of pyrazine dithiol reducing agents, and particularly for the preparation of pyrazine dithiol reducing agents linked to a solid or for the preparation of pyrazine dithiol reducing agents conjugated to a biological molecule.

The invention further relates to the pyrazine dithiane compounds and salts thereof of formula II which are the oxidized forms of the pyrazine dithiols of formula I:

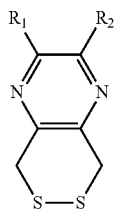

wherein $R_1$ and $R_2$ are as defined in formula I.

In specific embodiments of formula I or II
$R_1 = R_2$;
$R_1$ and $R_2$ are both hydrogen;
$R_1$ and $R_2$ are both methyl groups;
$R_1$ and $R_2$ are both —CN;
$R_1$ and $R_2$ are both —$NH_2$;
$R_1$ and $R_2$ are both —$N(R_6)_2$, where $R_6$ is hydrogen or alkyl and at least one $R_6$ is alkyl having 1-3 carbon atoms;
$R_1$ and $R_2$ are both —$CH_2$—$NH_2$;
$R_1$ and $R_2$ are both —$CH_2$—SH; or
$R_1$ and $R_2$ are both —$CH_2$—S—$COR_7$, where $R_7$ is an alkyl group having 1-6 (preferably 1-3) carbon atoms.

In specific embodiments of formula I or II:
$R_1$ and $R_2$ are different groups;
$R_1$ is hydrogen and $R_2$ is a group other than hydrogen;
$R_1$ is hydrogen and $R_2$ is —$NH_2$; or
$R_1$ is hydrogen and $R_2$ is —$CH_2$—$NH_2$.

In specific embodiments of formula I, $R_1$ and $R_2$ take any of the values above and
each $R_3$ is hydrogen; or each $R_3$ is —$COR_7$, where $R_7$ is an alkyl group having 1-6 (preferably 1-3) carbon atoms.

In specific embodiments of formula I, one or both of $R_1$ and $R_2$ are or contain an alkoxyalkyl group.

In a specific embodiment, dithiane compounds of the invention of formula II exclude the compound in which $R_1$ and $R_2$ are both hydrogen.

In specific embodiments of formulas I and II, $R_1$ and $R_2$ are groups other than divalent linker groups.

In specific embodiments of formulas I and II one of $R_1$ or $R_2$ are divalent linkers.

In specific embodiments, the dithiol of formula I is immobilized on a solid. In specific embodiments, the dithiol of formula I is immobilized on a solid via a divalent linker. In specific embodiments, the dithiol of formula I is conjugated to a biological molecule. In specific embodiments, the dithiol of formula I is conjugated to a biological molecule via a divalent linker.

In specific embodiments, the dithane of formula II is immobilized on a solid. In specific embodiments, the dithiane of formula II is immobilized on a solid via a divalent linker. In specific embodiments, the dithiane of formula II is conjugated to a biological molecule. In specific embodiments, the dithane of formula II is conjugated to a biological molecule via a divalent linker.

In specific embodiments, at least one of $R_1$ and $R_2$ is a —R-$[L]_a$—R'-T group (where —R-$[L]_a$—R'— is a divalent linker) where T represents a surface or a biological molecule, L is a spacer group, where a is 0 or 1 to indicate that the spacer is optional, and R and R' are chemical moieties functioning for bonding between the dithiol or dithiane, the spacer, if present, and T.

In specific embodiments, at least one of $R_1$, and $R_2$ is a —R-$M_a$-$IR_L$ group where —$R_L$ represents a reactive group, including a latent reactive group, L is a spacer group, where a is 0 or 1 to indicate that the spacer is optional, and R is a chemical moiety functioning for bonding between the dithiol or dithiane, and the spacer, if present, and $R_L$. Note that reaction of $R_L$ with an appropriate surface group or with an appropriate group of a biological molecule functions to immobilize to the surface or to conjugate to the biological molecule to form an —R-L-R'-T. A reactive group is selected for selective reaction with a selected surface group or with a selected functional group (e.g., —OH, —COOH, —$NH_2$ or the like) on a biological molecule. A latent reactive group is a group that can be activated for such reaction immobilization or conjugation reaction. An exemplary latent reactive group is a reactive group that is protected with a selectively removable protecting group and the latent reactive group is selectively activated for reaction by removal of the protecting group.

The invention further provides methods for preventing or reducing the oxidation of one or more sulfhydryl groups in a biological molecule, particularly a peptide or protein, in vivo or in vitro by contacting the biological molecule with one or more pyrazine dithiols of formula I. In a specific embodiment, an S-acylated pyrazine dithiol of formula I, is employed and is activated chemically or enzymatically by removal of a S-acyl group prior to or at about the same time as the peptide, protein (or other biological molecule) is contacted. In specific embodiments, the invention provides a method for preventing or reducing the formation of disulfide bonds or for cleaving already-formed disulfide bonds in or between one or more molecules containing sulfhydryl groups or disulfide bonds by contacting the one or more molecules with one or more pyrazine dithiols of formula I. In a specific embodiment, an S-acylated dithiol of formula I is employed and is activated chemically or enzymatically by removal of a S-acyl group prior to or at about the same time as the one or more molecules are contacted. In preferred methods of the invention, the pyrazine dithiol is BMMP.

In a more specific embodiment, the invention provides a method of regulating a biological activity of a protein wherein said biological activity is associated with the presence or absence of a sulfhydryl group or the formation or cleavage of a disulfide bond. In this method, a pyrazine dithiol of this invention is employed to prevent or reduce the oxidation of one or more sulfhydryl groups in a protein or to prevent or reduce the formation of a disulfide bond or to cleave an already-formed disulfide bond. In preferred embodiments of the invention, the pyrazine dithiol is BMMP.

The invention further relates to reagent kits which comprise one or more pyrazine dithiols of formula I individually packaged therein in selected amounts for use as a reducing agent. More specifically, such kits are for preventing or reducing disulfide bond formation or for cleaving disulfide bonds. Reagent kits may further comprise one or more solvents or other reagents for carrying out a reduction. In specific embodiments, the pyrazine dithiol is BMMP. In other embodiments, the pyrazine dithiol is S-acylated BMMP.

Additional embodiments of the invention will be apparent from a review of the drawings, detailed description and the examples herein.

BRIEF DESCRIPTION OF THE FIGURES

FIG. 3A shows reduction of Papain Cys25-S—S—CH3 where $k_{obs}^{BMMP}/k_{obs}^{DTBA}$=1.2 and $k_{obs}^{BMMP}/k_{obs}^{DTT}$=13.1. FIG. 3B shows reduction of Creatine kinase Cys283-S—S—I-glutathione where $k_{obs}^{BMMP}/k_{obs}^{DTBA}$=6.8 and $k_{obs}^{BMMP}/k_{obs}^{DTT}$=5.8.

DETAILED DESCRIPTION OF THE INVENTION

Dithiols (like DTBA and DTT, see Table 1) that form six-membered cyclic disulfides are potent reducing agents, reflecting a balance between the high enthalpic stability of the incipient ring and the low entropic loss for its formation [19, 25]. A thiol reducing agent having thiol pKa close to physiological pH (which is pH 7.365 in human blood) is of interest. This invention is based at least in part on the finding that 2,3-bis(mercaptomethyl)pyrazine (BMMP, Table 1) exhibits low thiol pKa values. A pH titration monitored by UV spectroscopy revealed the $pK_a$ values for BMMP to be 7.6±0.1 and 9.0±0.1. These pKa values are significantly lower than those of DTT and DTBA (Table 1) [28, 23]. Moreover, the lower of BMMP's two thiol pKa values is closer to physiological pH than any known dithiol-based reducing agent [8]. BMMP is an exemplary pyrazine dithiol. The desirable low thiol pKa is believed due at least in part to the presence of the electron withdrawing pyrazine group and the limitation on rotation of a bond between the two thiol groups.

BMMP was also found to be a potent reducing agent. The equilibrium reaction between reduced BMMP and oxidized DTT favors those species (rather than oxidized BMMP and reduced DTT) by −1.2 kcal/mol, which corresponds to a reduction potential of $E^\sigma$=(−0.301±0.003) V (Table 1) for oxidized BMMP. This $E^\sigma$ value is slightly less negative than both DTT and DTBA, and is believed to result from the decreased enthalpic stability imparted by the two sp2-hybridized carbons in its six-membered ring [25]. BMMP is, however, a much more potent reducing agent than common monothiols such as β-mercaptoethanol (βME), cysteamine, and L-glutathione [16,30]. To probe this difference, oxidized βME (βMEox) was equilibrated with a slight excess of reduced BMMP for 24 h. Analysis by HPLC revealed the complete reduction of β MEox.

Singh and Whitesides [11] put forth N,N'-dimethyl-N,N' bis(mercaptoacetyl)hydrazine (DMH; Table 1) as a faster disulfide reducing agent than DTT.[21] Notably, their reported pKa=7.6 (8.9) and $E^\sigma$=−0.300 V values for DMH are indistinguishable from those of BMMP (Table 1). The $E^\sigma$ value of DMH was corrected subsequently by the authors to be −0.272 V [19], which is more consistent with its forming an 8-membered ring upon oxidation. The pKa value of DMH has not been examined again. Accordingly, DMH was synthesized to reexamine its properties and utility. The value observed in the present work of $E^\sigma$=(−0.262±0.003) V for DMH was even higher than that of reported earlier [19] and confirms that DMH is a markedly weaker reducing agent than is BMMP, DTBA, or DTT (Table 1). Likewise, the value of pKa=8.0±0.1 (Table 1) measured in the present work is higher than that reported earlier [11], but is consistent with values reported for mercaptoacetamido groups [9, 22, 38].

Figure 2A:
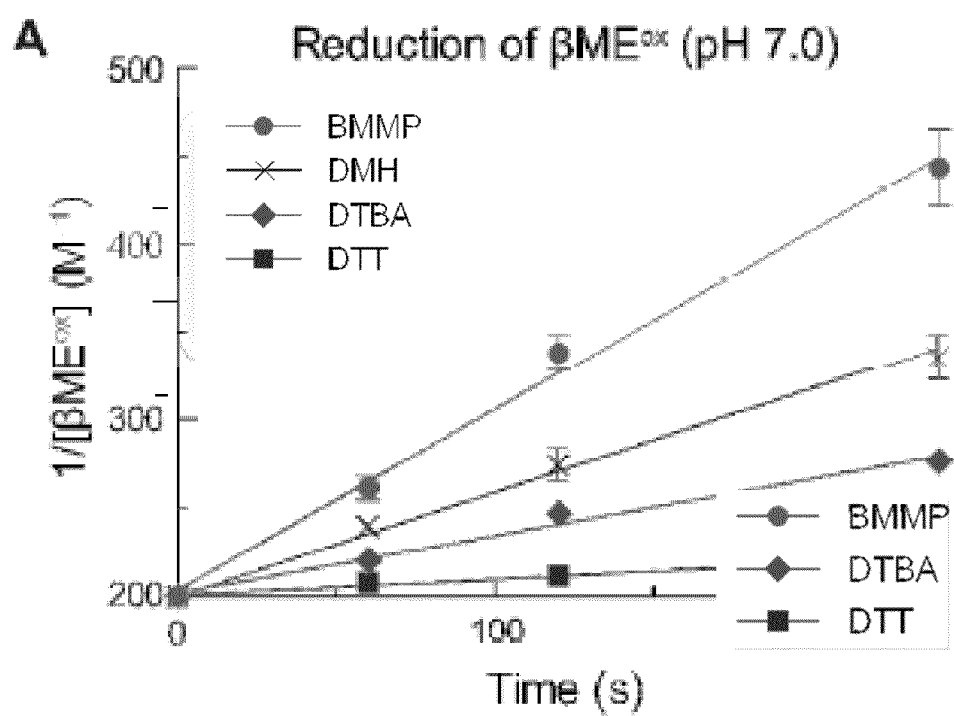
FIGS. 2A and 2B are graphs showing the time course for the reduction of βMEox (5 mM) by BMMP, DMH, DTBA, or DTT (5 mM) in buffered water (50 mM sodium phosphate buffer) at pH 7.0 (FIG. 2A) and (50 mM sodium acetate buffer) pH 5.0 (FIG. 2B). At pH 7.0, $k_{obs}^{BMMP}/k_{obs}^{DMH}$=1.8, $k_{obs}^{BMMP}/k_{obs}^{DTBA}$=3.2 and $k_{obs}^{BMMP}/k_{obs}^{DTT}$=11.4. At pH 5.0, $k_{obs}^{BMMP}/k_{obs}^{DTBA}$=3.6 and $k_{obs}^{BMMP}/k_{obs}^{DTT}$=14.1.
Figure 2B:
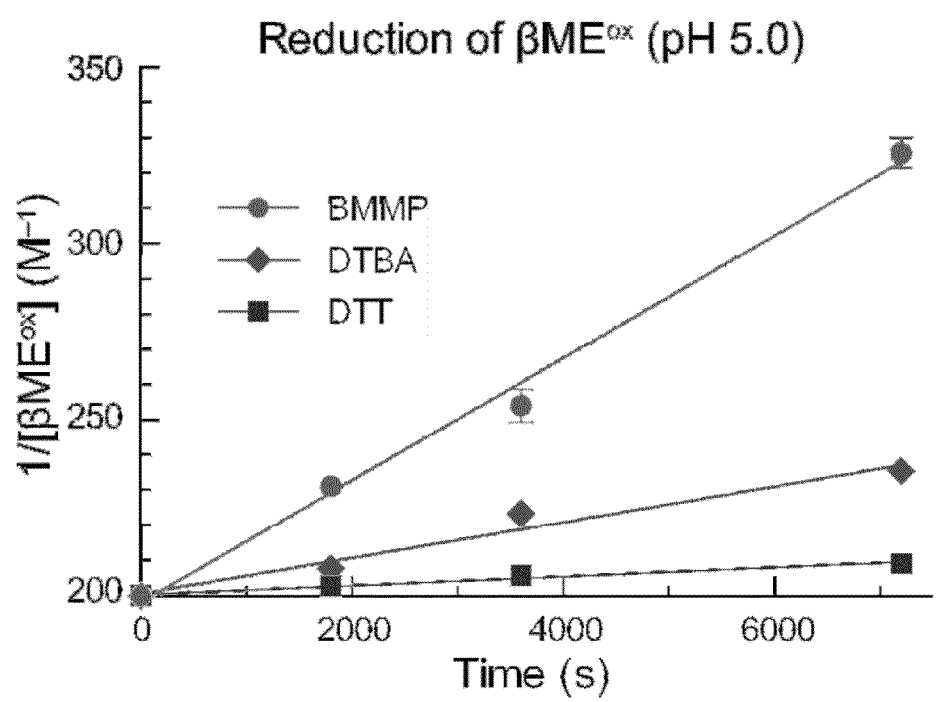

The reactivity of BMMP with relevant disulfide bonds was assessed. At pH 7.0, BMMP reduced the disulfide bond in βMEox 11-fold faster than did DTT and 3-fold faster than did DTBA (FIG. 2A). Commensurate with their pKa values, DMH reduced βMEox faster than did DTT or DTBA but slower than did BMMP. At pH 5.0, BMMP reduced βMEox 14-fold faster than DTT and 4-fold faster than did DTBA (FIG. 2B). The observed rate of reduction for BMMP at pH 5.0 was comparable to that for DTT at pH 7.0, (see Examples) highlighting the extended pH-range at which BMMP can be utilized effectively.

Figure 3A:
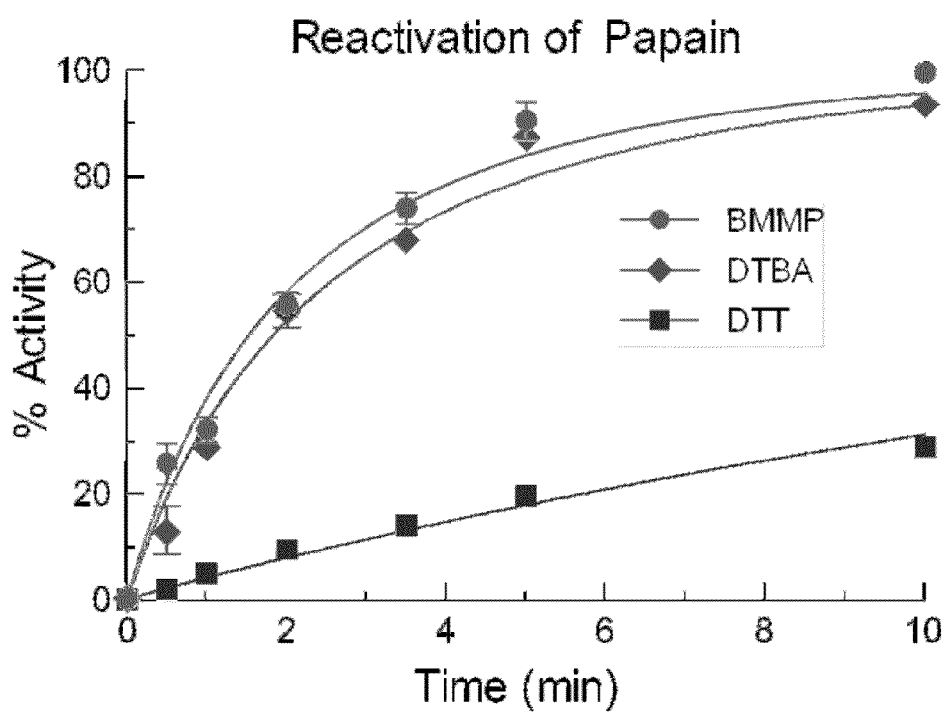
FIGS. 3A and 3B are graphs showing them time-course for the reduction of a mixed disulfide in proteins in 0.10 M imidazole-HCl buffer, pH 7.0, containing EDTA (2 mM).

The ability of BMMP to reduce disulfide bonds in two proteins was assessed. Papain is a cysteine protease that contains an active-site sulfhydryl group (Cys25) that needs to be in a reduced state for catalysis [31]. Treatment with S-methyl methanethiosulfonate generates an active-site mixed disulfide that results in complete loss of enzymatic activity [32]. This loss in activity, however, is reversible upon treatment with a disulfide reducing agent. BMMP reduced the mixed disulfide in papain 13-fold faster than did DTT and at a rate comparable to that of DTBA (FIG. 3A) [23].

Creatine kinase, like papain, is an enzyme that contains a thiol group (Cys283) that needs to be in a reduced state for catalytic function [33-36]. When treated with oxidized L-glutathione, the resulting mixed-disulfide eliminates its enzymatic activity. The ability of DTBA to reduce this disulfide bond was not enhanced resulting in a reaction rate comparable to that of DTT [23]. It is believed that the lack of enhancement was due to unfavorable Coulombic interactions because DTBA is cationic near neutral pH.

Figure 3B:
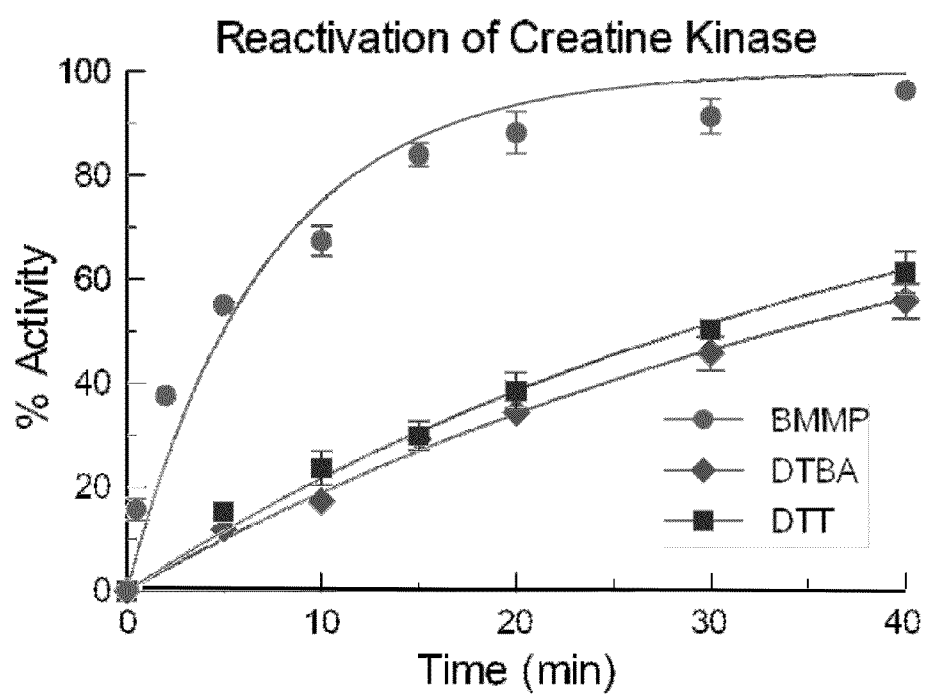

In contrast to DTBA, BMMP is not cationic near neutral pH. (For example, the pKa of the conjugate acid of 2,5-dimethylpyrazine is 2.1 [37]). Indeed, unfavorable Coulombic interactions were not apparent with BMMP, which was found to reduce the mixed disulfide in creatine kinase 6-fold faster than did DTT and 7-fold faster than did DTBA (FIG. 3B).

Thus, pyrazine dithiol-reducing agents of the invention exhibit enhanced reactivity under biological conditions. The pyrazine ring of these agents is believed to fuel this enhanced performance without Coulombic consequences. The depressed thiol pKas of the pyrazine dithiols extend the pH range at which disulfide bonds can be reduced efficiently. These attributes render pyrazine dithiols attractive reagent for the reduction of disulfide bonds under the solution conditions encountered in chemical biology.

BMMP is an exemplary reducing agent of this invention. The invention more generally relates to dithiol reducing agents useful, in particular, for the reduction of disulfide bonds, and to their corresponding oxidized counterparts as well as salts thereof as shown in Formulas I and II. Reducing agents of the invention include compounds of formula I above as well as such agents immobilized on surfaces or conjugated to biological molecules. Reducing agents and salts thereof the invention also include compounds of formula I above which have a reactive or latent reactive group useful for immobilization of the reducing agent on a surface or for conjugation to other chemical species including biological molecules. Oxidized forms of the reducing agents of this invention and salts thereof can similarly contain a reactive group or be immobilized or conjugated to other chemical species including biological molecules.

TABLE 1

Physical Properties of Exemplary Dithiol Reducing Agents

| Thiol Reducing Agent | Thiol p$K_a$ | Disulfide $E^{o'}$ |
|---|---|---|
| 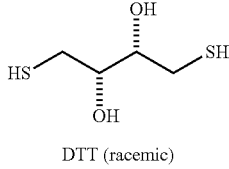 DTT (racemic) | 9.2 (10.1)$^a$ | −0.327 V$^b$ |
| 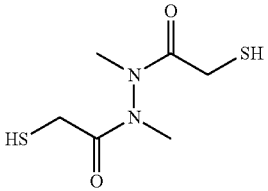 DMH | 8.0 ± 0.2 (9.1 ± 0.1)$^c$ | −0.262 ± 0.004 V$^c$ |
| 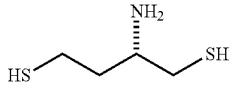 DTBA | 8.2 (9.3)$^d$ | −0.317 V$^d$ |
| 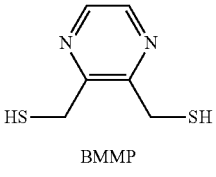 BMMP | 7.6 ± 0.1 (9.0 ± 0.1)$^c$ | −0.301 ± 0.003 V$^c$ |

$^a$Value are from ref. 11.
$^b$Value is from ref. 19.
$^c$Values are from this work.
$^d$Values are from ref. 23.

In specific embodiments, the dithiol (Formula I) and its corresponding oxidized forms (Formula II) of this invention is substituted with a reactive group which allows its coupling to a biological species or to a surface either directly or indirectly through a spacer moiety. In specific embodiments, the reactive group is a latent reactive group, such as a protected group which can be selectively activated for reaction for coupling of the compound directly or indirectly via a linker or spacer group to a T species, including a surface or other chemical species. In specific embodiments, —$R_L$ is or carries a reactive group or latent reactive group which reacts or can be activated (e.g., by deprotection) to react with one or more of an amine group, a carboxylic acid group, a sulfhydryl group, a hydroxyl group, an aldehyde or ketone group, an azide group, an activated ester group, a thioester group, or a phosphinothioester group or reacts with one reactive group of a homobifunctional or a heterobifunctional crosslinking reagent. In specific embodiments, when the reactive group is a sulfhydryl group, both of $R_3$ are acyl groups.

In specific embodiments, reactive groups are latent reactive groups which are protected amine groups, protected carboxylic acid groups, protected sulfhydryl groups, protected hydroxyl groups, or protected aldehyde or ketone groups. Protective groups, for various reactive groups are known in the art, for example as described in Wutts, P. G. and Greene, T. (2007) Green's Protecting Groups in Organic Synthesis (Fourth Edition) John Wiley & Sons, N.Y. This reference is incorporated by reference herein for its description of protective groups for a given reactive group and for methods of protecting reactive groups and methods for removing such protective groups. One of ordinary skill in the art can select from among known alternatives a protective group appropriate for a given reactive group under given conditions.

Amine-protective groups include among others: t-butyloxycarbonyl(BOC), 9-fluorenylmethyloxycarbonyl (FMOC), acetyl, benzyl, carbamate, p-methoxyphenyl, tosyl, 4-nitrophenylsulfonyl, or 4-aminophenyl sulfonyl. Carboxylic acid-protective groups include among others, esters (e.g., alkyl or aryl esters of the carboxylic acid), silyl esters, or orthoesters. Hydroxyl-protecting groups include among others, acyl groups (e.g., acetyl, benzoyl), beta-methoxyethoxymethyl ether, dimethoxytrityl, methoxytrityl, methoxymethyl ether, p-methoxybenzyl ether, pivaloyl, silyl ethers, methyl ethers or ethoxyethyl ethers.

In specific embodiments, the dithiol and corresponding oxidized forms of this invention is immobilized onto a surface via a linker group —R-[L]$_a$R'—. In specific embodiments, the dithiol of this invention is an S-acylated dithiol of this invention immobilized onto a surface via a linker group —R-[L]$_a$R'—. In specific embodiments, the dithiol of this invention is conjugated to a biological molecule via a linker group —R-[L]$_a$R'—. In specific embodiments, the dithiol of this invention is an S-acylated dithiol of this invention conjugated to a biological molecule via a linker group —R-[L]$_a$R'—. In specific embodiments, the biological molecule is a peptide or protein, a carbohydrate or a nucleic acid. In specific embodiments, the biological molecule is a ligand or substrate that binds to a second biological molecule, particularly where the second biological molecule is a peptide or protein.

The invention provides dithiol reducing agents and their oxidized forms immobilized on surfaces. Immobilized reducing agents can be used as recognized in the art to reduce all types of disulfides, particularly biological disulfides, including those in or between proteins. Separation of reduced species from the reducing agent requires less effort and is more efficient. Immobilized reducing agent can be regenerated (from their immobilized oxidized forms) as is known in the art and reused multiple times. The immobilized dithiols can be S-acylated (particularly S-acetylated) for chemical or enzymatic activation prior to use. In specific embodiments, where the reducing agent contains an amine group, the S-acylated dithiol is also N-acylated. For example, S-acylated dithiol can be deacylated employing hydroxyl amine or other such art-recognized deacylating reagents. The dithiol reducing agents can be immobilized on any appropriate surface by any immobilization method known in the art. In specific embodiments, dithiol reducing agents can be covalently attached to a surface by reaction of a reactive group on the reducing agent with a reactive group on the surface. Alternatively, a homo- or heterobifunctional crosslinking reagent such as are known in the art can be employed to immobilize the dithiol reducing agent of this invention on the surface.

S-acylated dithiols of this invention function as precursors of the dithiol reducing agents hereof which can be activated as reducing agents by removal of the S-acyl groups to generate sulfhydryl groups. S-acylated dithiols of this invention can be activated by removal of acyl groups as is known in the art, for example by treatment with hydroxylamine or by treatment with acidic methanol. Of particular interest is activation of S-acylated dithiol with esterases, including carboxylesterases. Useful esterases that function for removal of S-acyl groups are known in the art, such as those esterases that are associated with the removal of SATE (S-acyl-2-thioethyl) protection [39-41].

In a specific embodiment, S-acylated precursors of reducing agents herein are activated in vivo, e.g., inside of cells by the action of esterases therein. For example, these precursors can be activated inside of mammalian cells by the action of mammalian esterase. More specifically, these precursors can be activated inside of human cells by the action of human esterases. It is noted that such esterase may also be employed in vitro for activation of S-acylated precursors.

The invention provides dithiol reducing agents of formula I and oxidized forms thereof of Formula II conjugated to various chemical species T which can be biological molecules, such as proteins, carbohydrates or nucleic acids; labels or tags, such as radiolabels, isotopic labels or fluorescent labels or ligands or substrates that selectively bind to target the conjugate to species which are to be selectively reduced. In specific embodiments, the reducing agents of this invention can be targeted for reduction of a specific protein employing such selective ligands or substrates. In specific embodiments, ligands can be mono- or disaccharides, e.g., glucose or fructose. In specific embodiments, ligands can be sialic acid or analogues thereof (see, exemplary sialic acid analogues in ref. 42). Reference 42 is incorporated by reference herein in its entirety for its description of sialic acid analogues.

As noted above, dithiol reducing agents of this invention optionally carry —[L]$_a$—R$_L$ groups (or simply —R$_L$ groups where a is 0) which function for immobilization, optionally spacing, and/or conjugation to surfaces or other chemical or biological moieties, i.e., T.

In specific embodiments, —R$_L$ is a reactive group which reacts with one of: an amine group, a carboxylic acid group, a sulfhydryl group, a hydroxyl group, an aldehyde or ketone group, an azide group, an activated ester group, a thioester group, or phosphinothioester, or reacts with one reactive group of a homobifunctional or a heterobifunctional crosslinking reagent. In another embodiment, —R$_L$ is a reactive group that reacts with two or more of the above listed groups. In another embodiment, —R$_L$ is or contains a reactive group that can be ligated to a peptide or protein by a peptide ligation method. In specific embodiments, —R$_L$ is or contains an amine group, a carboxyl group or ester thereof, an activated ester group, an azide, a thioester, or a phosphinothioester. In another embodiment, —R$_L$ is or contains a latent reactive group which can be selectively activated for reaction.

In general the optional spacer moiety -L- is compatible with any reactive group present in the compound of formula I or II (e.g., does not detrimentally affect reactivity of the reactive group) and the spacer itself is not reactive with the compounds to be conjugated to the agent or surfaces on which the agent is to be immobilized. In specific embodiments, the spacer moiety contains from 3-30 atoms, more preferably 3-20 atoms, (typically C, O, S and/or N atoms which may be substituted with H or non-hydrogen substituents), including residues from the reactive group), and optionally contains one or more carbon-carbon double bonds, and/or a 5- to 8-member alicyclic, a 5- to 8-member heterocyclic, a 6- or 10-member aryl or a 5- or 6-member heteroaryl ring. Carbon atoms in the spacer or linker are optionally substituted with one or more hydroxyl groups, oxo moieties (=O), or halogens (e.g., F). Nitrogen groups in the spacer may be substituted with hydrogen and/or with C1-C3 alkyl groups. The spacer may contain a diol (>C(OH)—C(OH)<) moiety. The spacer may be selectively cleavable by change of conditions (e.g., pH change), addition of a cleavage reagent, or photoirradiation (e.g., UV irradiation). In specific embodiments, a cleavable spacer includes a diol moiety which is selectively cleavable by treatment for example with periodate, an ester moiety, which is selectively cleavable by treatment with hydroxylamine, or a sulfone moiety (—SO$_2$—) which is selectively cleavable under alkaline conditions.

In specific embodiments, —R$_L$ is a reactive group for ligation, bonding or crosslinking to an amino acid, peptide or protein.

A variety of spacer moieties -L- are known in the art to be useful for bioconjugation or immobilization. In specific embodiments, the linker may be a single bond. All such art known spacer moieties can be employed in this invention, if compatible with the chemistry of the dithiol reducing agent and the species or surface to which the agents is to be conjugated or upon which it is to be immobilized. The spacer moiety should not detrimentally affect reactivity of chosen reactive groups and should not themselves react with the dithiol reagent, any reactive group employed for conjugation or immobilization or with the surface or species to be conjugated to the reagent.

In specific embodiments —R-L-R'— is selected from the following divalent moieties:

—Y1-L1-Y3-, where Y1 and Y3 are optional and if present may be the same or different;

—Y1-L1-L2-Y3-, where Y1 and Y3 are optional and if present may be the same or different and L1 and L2 are different; or —Y1-L1-[L2-Y2]y-L3-Y3-, where Y1 and Y3 are optional, Y1, Y2 and Y3, if present, may be the same or different, L1 and L3 are optional and L1, L2 and L3 if present may be the same or different and y is an integer indicating the number of repeats of the indicated moiety where y can be 0 (group not present) or 1-20;

wherein each L1-L3 is independently selected from an optionally substituted divalent aliphatic, alicyclic, heterocyclic, aryl, or heteroaryl moiety having 1 to 30 atoms and each Y1, Y2 and Y3 is independently selected from: —O—, —S—, —NR$_c$—, —CO—, —O—CO—, —CO—O—, —OCOO—, —CO—NR$_c$—, —NR$_c$—CO—, —NR$_c$—CO—NR$_c$—, —OCO—NR$_c$—, —NR$_c$—CO—O—, —N=N—, —N=N—NR$_c$—, —CO—S—, —S—CO—, —SO$_2$—, —SO$_2$—NR$_c$—, —SO$_2$—NR$_c$—CO—, —NR$_c$—CS—NR$_c$—, or —CR$_c$(OH)—CR$_c$(OH)—, where R$_c$ is hydrogen or C1-C3 alkyl, where Y1, Y2, Y3 independently are —R— or —R'—.

In specific embodiments, y is 1-12 and L1-L3 are selected from:

—(CH$_2$)y- (an alkylene) wherein one or more, and preferably 1-4, carbons of the alkylene are optionally substituted with one or more non-hydrogen substituents selected from halogens, C1-C3 alkyl groups or hydroxyl groups, preferred y are 2-6;

a cycloalkylene, having a 3-8-member ring wherein one or more, and preferably 1-4, carbons of the cycloalkylene are optionally substituted with one or more non-hydrogen substituents selected from halogens, C1-C3 alkyl groups or hydroxyl groups, including among others a 1,4-cyclohexylene, a 1,3-cylohexylene, a 1,2-cyclohexylene; a 1,3-cyclopentylene, each of which is optionally substituted;

a phenylene, wherein 1-4 of the ring carbons are optionally substituted with one or more non-hydrogen substituents selected from halogens, C1-C3 alkyl groups, nitro group, cyano group, or hydroxyl groups, including a 1,4-phenylene, a 1,3-phenylene or a 1,2-phenylene, each of which is optionally substituted;

a naphthylene, wherein 1-8 of the ring carbons are optionally substituted with one or more non-hydrogen substituents selected from halogens, C1-C3 alkyl groups, nitro group, cyano group, or hydroxyl groups, including a 2,6-naphthylene, a 2,7-naphthylene, a 1,5-naphthylene, or a 1,4-naphthylene moiety, each of which is optionally substituted;

a biphenylene, wherein 1-8 of the ring carbons are optionally substituted with one or more non-hydrogen substituents selected from halogens, C1-C3 alkyl groups or hydroxyl groups, including a 1,4'-biphenylene, a 1,3'-biphenylene or a 1,2'-biphenylene, each of which is optionally substituted;

an alkenylene, i.e., a divalent alkylene group, containing one or more, preferably 1 or 2 double bonds and having 2-12 and preferably 2-8 carbon atoms, wherein one or more, and preferably 1-4, carbons are optionally substituted with one or more non-hydrogen substituents selected from halogens, C1-C3 alkyl groups or hydroxyl groups, including among others, —CH═CH— and —CH═CH—CH═CH— which are optionally substituted;

a heterocyclene (i.e., a divalent heterocyclic moiety) having a 3-8-member ring with 1-3 heteroatoms, selected from N, O or S, wherein one or more, and preferably 1-4 carbons, or where feasible heteroatoms, of the heterocyclene are optionally substituted with one or more non-hydrogen substituents selected from halogens, C1-C3 alkyl groups, nitro groups, or hydroxyl groups, including among others a 2,4-3H-azepinylene moiety, a piperidinylene (e.g., a 1,4-piperidinylene), a piperazinylene (e.g., a 1,4-piperazinylene), a triazolidinylene (a divalent triazolidinyl) or a triazolylene (a divalent triazolyl) each of which is optionally substituted; or a heteroarylene (i.e., a divalent heteroaryl moiety) having a 5- or 6-member heteroaryl ring having 1-3 heteroatoms selected from N, O or S, wherein one or more, and preferably 1-2 carbons, or where feasible heteroatoms, of the heteroarylene are optionally substituted with one or more non-hydrogen substituents selected from halogens, C1-C3 alkyl groups, nitro groups, or hydroxyl groups, including among others a pyridylene (e.g., 2-5-pyridylene), imidazolylene (e.g., 2,5-imidazolylene, 4,5-imidazolylene), each of which is optionally substituted.

In additional embodiments, the spacer (-L-) is an alkoxyalkyl spacer (a divalent alkoxyalkylene moiety) which can generally be described as an alkylene moiety where one or more of the —$CH_2$— groups are replaced with a oxygen. More specifically, -L- is selected from —[$(CH_2)y_a$-O]$_a$—, —[$(CH_2)y_a$-O]$_a$—$(CH_2)_{ya+1}$, —O—[—$(CH_2)y_a$-O]—, or —O—[$(CH_2)y_a$-O]$_a$—$(CH_2)_{ya+1}$, where each $y_a$ or $y_{(a+1)}$ is independently 1-4 and a is 1-6, and preferably 1-3. Specific alkoxyalkyl spacers include, among others:

—[$(CH_2)y$-O]$_{1-6}$—, where each y is 2 or 3;
—[$(CH_2)y$-O]$_{1-6}$—$(CH_2)_{1-6}$—, where each y is 2 or 3;
—O—[$(CH_2)y$-O]$_{1-6}$—$(CH_2)_{1-6}$—, where each y is 2 or 3;
—O—[$(CH_2)y$-O]$_{1-6}$—, where each y is 2 or 3;
—$(CH_2)_{y1}$—O—$(CH_2)_{y2}$—O—$(CH_2)_{y3}$—O—, —O—$(CH_2)_{y1}$—O—$(CH_2)_{y2}$—O—$(CH_2)_{y3}$—O—, —O—$(CH_2)_{y1}$—O—$(CH_2)_{y2}$—O—$(CH_2)_{y3}$—, or —$(CH_2)_{y1}$—O—$(CH_2)_{y2}$—O—$(CH_2)_{y3}$—, where y1, y2 and y3 are (1) all the same and are 1-6, or (2) not all the same and are 1-6;
—$CH_2$—O—$CH_2$—;
—$CH_2$—$CH_2$—O—$CH_2$—$CH_2$—;
—$CH_2$—$CH_2$—$CH_2$—O—$CH_2$—$CH_2$—$CH_2$—; or
—$CH_2$—$CH_2$—O—$CH_2$—$CH_2$—O—$CH_2$—$CH_2$—.

Exemplary —R-L-R'— include: —CO—O—$(CH_2)y$-O—CO—, —O—OC—$(CH_2)y$-O—CO—, —O—OC—$(CH_2)y$-CO—O—, —O—$(CH_2)y$-CO—O—, or —O—$(CH_2)y$-O—CO—, —OC—NH—$(CH_2)y$-NH—CO—, —OC—NH—$(CH_2)y$-CO—NH—, —NH—OC—$(CH_2)y$-CO—NH—, —CO—O—$(CH_2)y$-CO—NH—, —O—CO—$(CH_2)y$-CO—NH—, —CO—O—$(CH_2)y$-NH—CO—, or —O—CO—$(CH_2)y$-NH—CO—O—, where y is 2-10 or 2-6.

In further embodiments, —R-[L]$_a$—R$_L$ is selected from:
—CO—NH—CRaRb-[CO—NH—CRaRb]$_a$—COOH, where a is 1-6;
—COO—CRaRb-[CO—NH—CRaRb]$_a$—COOH, where a is 1-6;
—O—CO—NH—CRaRb-[NH—CO—CRaRb]$_a$—COOH, where a is 1-6;
—CO—NH—CRaRb-[CO—NH—CRaRb]$_a$—$NH_2$, where a is 1-6;
—COO—CRaRb-[CO—NH—CRaRb]$_a$—$NH_2$, where a is 1-6;
—O—CO—NH—CRaRb-[NH—CO—CRaRb]$_a$—$NH_2$, where a is 1-6;
—CO—NH—CRaRb-[CO—NH—CRaRb]$_a$—X4, where a is 1-6;
—COO—CRaRb-[CO—NH—CRaRb]$_a$—X4, where a is 1-6;
—O—CO—NH—CRaRb-[NH—CO—CRaRb]$_a$—X4, where a is 1-6;
—Y4-CRaRb-[W—CRaRb]$_a$—X4, where W is —NH—CO— or —CO—NH—, where a is 1-6; and where:

—X4 is a functional group that reacts with one or more of an amine group, a carboxylic acid group or ester thereof, a sulfhydryl group, a hydroxyl group, an azide group, a thioester group, a phosphinothioester group, an aldehyde group or a ketone group of an amino acid, peptide or protein; and —Y4- is —O—, —S—, —NH—, —CO—, —$CO_2$—, —O—CO—, —CO—O—, —CO—NR$_c$—, —NR$_c$CO—, —NR$_c$—CO—NR$_{c'}$—, —NR$_c$—CS—NR$_{c'}$—, —CO—S—, or —S—CO— and R$_c$ is hydrogen or a C1-C3 alkyl;

Ra and Rb are selected independently from hydrogen, a C1-C8 aliphatic group, an alicyclic, a heterocyclic, an aryl or a heteroaryl group, each of which is optionally substituted or Ra is hydrogen and Rb is a side-group or protected side-group of a proteinogenic amino acids or an amino acid selected from hydroxyproline, ornithine, or citrulline.

In specific embodiments, X and X4 are —$NH_2$, —COOH or an activated ester thereof, —SH, —$N_3$, —COH, —CO—CH═$CH_2$, —NH—CO—CH═CH, or —C≡CH.

In specific embodiments, —R$_L$ is a N-hydroxysuccinimidyl group or a sulfo-N-hydroxysuccinimidyl group.

T is a biological or chemical species or a surface to which a reducing agent is conjugated, typically via a spacer or linking moiety (-L-). T can be a biological molecule, which includes molecules derived from nature such as peptides, proteins, carbohydrates (e.g., mono-, di- and oligosaccharides), or nucleic acids (e.g., a nucleoside, a mono-, di- or polynucleotide, a DNA sequence or an RNA sequence) which may be isolated from nature or synthesized. T can be a biological or chemical species which is a ligand which binds to a biological molecule or which is a substrate for an enzyme. T can, for example, be a biological or chemical species which is anionic or cationic which will preferentially associate with a corresponding cationic or anionic portion, respectively, of a biological molecule, such as a peptide or protein to target the biological molecule and selectively target the reducing agent (or acylated precursor thereof) of this invention to the biological molecule to affect its biological activity.

In a particular embodiment, T is a pharmacophore of a selected biologically active species, particularly a pharmacophore associated with a selected peptide or protein or ligands thereof. As is known in the art, pharmacophore refers to the 3-D molecular features (structural and electronic features) necessary for interaction with a target biological species which can trigger or block a biological response. Pharmacophore modeling [43] represents one aspect of ligand-based drug design which can provide 3-D chemical moieties which interact with biological molecules (e.g., by binding or association therewith) and thereby affect biological function thereof.

In specific embodiments, dithiol and/or oxidized forms thereof of this invention can be immobilized on various surfaces including inorganic and organic surfaces. The surface may be among others that of a plate, a container (tube, bottle, etc.) which can, for example, be made of plastic or glass, a bead, particle, microparticle or nanoparticle. The surface may be a polymer, a co-polymer, a block co-polymer, a graft-copolymer or a resin each of which may be cross-linked. Polymeric materials include among others, agarose, poly(acrylamide) and co-polymers thereof, poly(methylmethacrylate) and co-polymers thereof, poly(hydroxyethyl methacrylate) and co-polymers thereof, poly(vinyltoluene) and co-polymers thereof, poly(styrene) and co-polymers thereof (e.g., poly(styrene/divinylbenzene) copolymers, poly(styrene/acrylate) co-polymers, poly(styrene/butadiene) co-polymers, poly(styrene/vinyltoluene) co-polymers). The surface may be that of a core-shell particle having a core of one material (e.g., one polymeric material) and a shell or coating of a different material (e.g., a coating polymers, such as poly(ethylene glycol), poly(vinyl alcohol), poly(acrylamide), poly(vinyl pyrrolidone), among others. A specific core-shell particle has a poly(styrene) core with a poly(hydroxyethyl methacrylate) shell.

The surface may be glass, quartz, silica, silica gel, alumina or other metal oxides, or inert metal such as gold (e.g., gold nanoparticles), again in the form among others of plates, beads or particles. The surface may be that of a magnetic, paramagnetic or superparamagnetic material.

The surfaces may contain reactive functional groups that derive from the material from which the particle is made (e.g., OH groups on glass, or amine groups of poly(acrylamide)) or the particles may be functionalized as is known in the art with reactive groups, for example, as noted above, including among others, amine groups, aldehyde or ketone groups, carboxyl groups, epoxides, hydrazides, hydroxyl, amide, sulfamyl groups, or activated esters, such as tosyl-, mesyl- or tresyl-activated esters or NHS esters.) Hermanson, G. T. (2008) Bioconjugate Techniques (Second Edition) Academic Press, N.Y., Chapter 14, pages 582-625 describes conjugation/immobilization of various chemical and biological species on surfaces and particles. This reference is incorporated by reference herein in its entirety for this description.

In a specific embodiment, one or more reducing agents of this invention is conjugated to a polymer (i.e., T is a polymer). In a specific embodiment, two or more molecules of reducing agent are conjugated to a polymer. In a specific embodiment, 10% or more or 25% or more of the monomer groups of a polymer are conjugated to a reducing agent of Formula I or its oxidized form of Formula II. In specific embodiments, the polymer carries one or more amino groups which can be conjugated, optionally but preferably via a spacer or linker, to a reducing agent or acylated precursor thereof of this invention. In specific embodiments, the polymer carries one or more amine, amide or ester side chains which can be conjugated to one or more reducing agents of this invention. Polymers useful for such conjugation include among many others, poly(lysine), poly(ornithine), poly(lysine ornithine), poly(aspartic acid), poly(glutamic acid), poly(acrylamide), poly(ethylene imine), poly(propylene imine), poly(allyl amine), poly(vinyl amine), poly(2-aminoethyl methacrylate), poly(methacrylate), poly(methyl methacrylate), poly(acrylate), poly(hydroxyethyl methacrylate), poly(methyl acrylate), poly(vinyl acetate) and copolymers including block copolymers thereof. Methods of conjugation as described in Hermanson, G. T. (2008) Bioconjugate Techniques (Second Edition) Academic Press, N.Y. can be employed or readily adapted for conjugation to polymers.

In specific embodiments, the dithiol reducing agents or dithiane precursors thereof are covalently attached to surfaces, in particular to resins, which may be in the form of beads or other particles or in the form of coatings on surfaces or particles. In specific embodiments, resins useful for immobilization of dithiol or dithianes of this invention include resins known and used in the art for solid-phase organic synthesis and/or for solid-phase peptide synthesis. A variety of such resins are known in the art are commercially available or can be prepared by methods that are well-known in the art. For example, such resins are or may be functionalized with amine, azide, carboxyl, sulfamyl, formyl, halogen, hydroxyl, mercapto, sulfonylchloride, sulfonic acid, or various activated ester groups for reaction with appropriate reactive groups attached to the dithiol or dithiane to immobilize the dithiol or dithiane. Resins are typically composed of a polymer matrix which may be cross-linked, such as polystyrene, and functional groups may be directly attached to the resin or attached to a linker groups, such as polyethylene glycol, which are in turn attached to the resin matrix. In some cases, resins may contain latent reactive groups (e.g., protected reactive groups) which must be activated before the dithiol or dithiane is immobilized. Useful resins for immobilization of dithiols or dithianes of this invention include among others, aminoalkyl resins, Rink amide resin, MBHA resins, indole resins, hydroxylamine resins, Sieber amide resins, PAL resins, sulfamyl-based resins, Wang resin, HMPA-AM resins, Merrifield resin, PAM resins, oxime resins, various safety-catch resins and the like. One of ordinary skill in the art can employ any such resins to immobilize the dithiols and dithianes of this invention using well-known methods or routine adaptation of such well-known methods. Albericio, F. and Tulla-Puche (ed) (2008) The Power of Functional Resins in Organic Synthesis (Wiley-Verlag) provides a description of various useful resins and methods of using such resins for immobilization of various chemical species. This reference is incorporated by reference herein in its entirety to illustrate what is known in the art concerning such resins, methods for their use and methods of immobilization that are useful in this invention.

The invention provides specific immobilized dithiol reducing agents and immobilized dithianes of formula I and II where one of $R_1$ or $R_2$ is $T_R$-$X_1$-L-CO—N($R_N$)—,
where:
$T_R$ is a surface including a resin,
L is a divalent spacer as described herein,
$R_N$ is hydrogen, or an alkyl or aryl group that is optionally substituted, and X1 is a single bond, —O—, —OCO—, —COO—, —NHCO—, —CONH—, —SO$_2$—NH—, —SO$_2$—NH—CO—, —NHCONH—, or —OCOO—. In a specific embodiment, R$_N$ is hydrogen. In specific embodiments, —X1-L- is —NHCO—(CH$_2$)r-, where r is 1-6 and r is preferably 2; or —X1-L- is —NHCO—CH$_2$CH$_2$OCH$_2$CH$_2$—.

In specific embodiments, compounds of this invention of formulas I, IA, IB and II contain a reactive functional group for attachment of the compound to a T species (as described herein, including chemical species, biological molecules, a polymer or a surface. The reactive functional group can, for example, be a group that reacts with an amine, a carbonyl, a carboxylate, a carboxylic ester, sulfamyl group (—SO$_2$—NH$_2$), or hydroxyl group. Generally, sulfhydryl reactive groups are less preferred as care must be taken to protect sulfhydryl groups on the reducing agent. Preferably such reactive groups react to conjugate the species under conditions such that the reducing agent substantially retains functionality and which do not substantially detrimentally affect biological activity of interest of the T species (if any). A variety of reactive groups useful for such coupling are known in the art and one of ordinary skill in the art can select among such known reactive groups to practice the methods of the present invention without undo experimentation.

An overview of bioconjugation methods that can be employed in the present invention is found in Hermanson, G. T. Bioconjugation Techniques (2nd Ed.) 2008 Academic Press/Elsevier London, UK. This reference also contains detailed descriptions of homobifunctional and heterobifunctional crossing linking reagents which can be employed for conjugation.

Amine-reactive groups are exemplified by a carboxylate group, a carboxylate ester group, an acid chloride group, an aldehyde group, an acyl azide group, an epoxide, an isothiocyanate group, an isocyanate group, an imidoester group or an anhydride group. Amines react with carboxylates in the presence of coupling reagents, such as carbodiimides. Amine-reactive groups include active carboxylic acid ester groups, such as succinimidyl ester groups or sulfosuccinimidyl ester groups (e.g., N—OH succinimidyl or N—OH sulfosuccinimidyl groups); haloalkyl ester groups, such as trifluoroalkyl ester groups and hexafluoroalkyl ester groups; halophenyl ester groups, particularly fluorophenyl and chlorophenyl ester groups, including penta- and tetrafluorophenyl ester groups, pentachlorophenyl ester groups; nitrophenyl ester groups, including 2-nitrophenyl, 4-nitrophenyl and 2,4-dinitrophenyl ester groups; as well as other substituted phenyl ester groups, including sulfodichlorophenol ester groups.

General conditions for carrying out reactions between amine-reactive groups and amino groups of an amino acid, peptide or protein are well known in the art and can be carried out by one of ordinary skill in the art without undue experimentation.

Although not preferred, sulfhydryl-reactive groups are exemplified by haloacetyl and haloacetamidyl groups, particularly iodoacetyl and bromoacetyl or corresponding acetamidyl groups, maleimide groups, haloalkyl groups, halobenzyl groups, acryloyl groups, epoxide groups, groups that undergo thiol-disulfide exchange, such as dipyridyl disulfide groups or 2,2'-dihydroxy-6,6'-dinaphthyldisulfide groups, or thiosulfate groups. General conditions for carrying out reactions between sulfhydryl-reactive groups and sulfhydryl groups are well known in the art and can be carried out by one of ordinary skill in the art without undue experimentation.

Carboxylate-reactive functional groups are exemplified by amines (e.g., employing a carbodiimide), hydrazine groups, hydrazide groups, sulfonylhydrazide groups, diazoalkyl groups, sulfamyl, diazoaryl groups, diazoacetyl groups, hydroxyl groups or sulfhydryl groups.

Hydroxyl-reactive functional groups are exemplified by isocyanate groups; epoxide groups; alkyl or aryl halide group, e.g., a halotrityl group; an activated carbamate group, an activated ester group (such as described above), N,N'-disuccinimidyl carbonate groups or N-hydroxysuccinimidyl chloroformate groups.

Aldehyde and ketone-reactive groups are exemplified by hydrazine groups and derivatives thereof including hydrazides, semicarbazides and carbohydrazides, and amino groups. Various methods for introduction of aldehyde and ketone groups into amino acids, peptides and proteins are known in the art.

Azide groups react with alkenyl or akynyl groups (in so-called Click reactions) to form triazolines or triazoles. Click reactions can be used to link a reducing agent of the invention with a T group or to a surface. Linkers formed in such reactions will include a triazoline or triazole moiety.

Phosphinothioesters react with azide groups as described in U.S. Pat. Nos. 6,972,320 and 7,256,259, and 7,317,129 and U.S. published application US 2010/0048866 to form amide bonds in a traceless Staudinger ligation. Phosphinothioesters can be prepared employing phosphinothiol reagents as also described in these references. Each of these references is incorporated by reference herein in its entirety for descriptions of such ligation reactions, methods of making azides and methods of making phosphinothioesters.

Aldehyde, ketone, azide activated esters groups, thioester, phosphinothiol groups are introduced by any art-known methods.

Homobifunctional crosslinking reagents contain two identical reactive groups separated by a spacer or linker moiety. Heterobifunctional crosslinking reagents contain two reactive groups with different selectively for reaction, e.g., an amine-reactive group and a sulfhydryl-reactive group separated by a spacer or linker moiety. Various homobifunctional and heterobifunctional crossing linkage reagents are known in the art and a number are commercially available from Pierce (Thermo Scientific), Rockford, Ill., Sigma-Aldrich, St. Louis, Mo. or Molecular Probes (Life Technologies), Eugene Oreg.

Useful homobifunctional crosslinking reagents include those carrying two amine-reactive groups, those carrying two carboxylate reactive groups, or those carrying two aldehyde or ketone reactive groups. Homobifunctional crosslinking reagents carrying sulfhydryl reactive groups are generally not preferred. Such reagents can be employed if appropriate sulfhydryl group protecting agents, such as acyl groups, are employed to prevent reaction with the sulfhydryl groups of the reducing agent.

Useful heterobifunctional crosslinking reagents include those carrying one of an amine-reactive group, a sulfhydryl reactive group, a carboxylate reactive group, or an aldehyde or ketone reactive group and one of a different reactive group selected from an amine-reactive group, a sulfhydryl reactive group, a carboxylate reactive group, or an aldehyde or ketone reactive group. Again heterobifunctional crosslinking reagents carrying sulfhydryl reactive groups are generally not preferred as noted above.

Homobifunctional and heterobifunctional crosslinking reagents can in general contain any spacer or linking moiety compatible with the reactive groups therein wherein the spacer or linker itself is not reactive with the compounds to be conjugated. In specific embodiments, disulfide moieties are not preferred in such spacers or linkers. In specific embodiments, the spacer or linking moiety typically ranges from 3-20 atoms (typically C, O, S and/or N atoms) in length (including residues from the reactive group), and optionally contain one or more carbon—carbon double bonds, and/or a 5- or 6-member alicyclic, heterocyclic, aryl or heteroaryl ring. Carbon atoms in the spacer or linker are often substituted with one or more hydroxyl groups, oxo moieties (=O), or halogens (e.g., F). Nitrogen groups in the linker may be substituted hydrogen or with C1-C3 alkyl groups. The spacer or linker may contain one or two —SO$_2$— moieties. The spacer or linker may be selectively cleavable by change of conditions (e.g., pH change), addition of a cleavage reagent, or photoirradiation (e.g., UV irradiation). In specific embodiments, a cleavable linker includes a cleavable linker contains a diol moiety which is selectively cleavable by treatment for example with periodate, an ester moiety, which is selectively cleavable by treatment with hydroxylamine, a sulfone moiety (—SO$_2$—) which is selectively cleavable under alkaline conditions.

Homobifunctional crosslinking reagents can be used, for example, to conjugate an amine group of an reducing agent or acylated precursor thereof with an amine functionality on a biological or chemical species T, polymer or a surface. Amine-reactive groups employed in homobifunctional crosslinking reagents include among others, activated ester groups, such as NHS esters (N-hydroxysuccinimide esters) or sulfo NHS esters (N-hydroxysulfosuccinimide esters), imidoester group, such as methylimidate salts, isothiocyanate groups and aryl halide groups, such as difluorobenzene derivatives. Amine-reactive homobifunctional include among others: dithiobis(succinimidylproprionate) [DSP] and its sulfo-NHS analog [DTSSP], disuccinimidyl suberate [DSS] and its sulfo-NHS analog [BS3], disuccinimidyl tartarate [DST] and its sulfo NHS analog [sulfo-DST], bis(2-succinimidyloxy-carbonyloxy)ethylsulfone [BSOCOES] and its sulfo-NHS analog [sulfo-BSOCOES], ethylene glycol bis(succinimidylsuccinate) [EGS] and its sulfo-NHS analog [sulfo-EGS], disuccinimidyl glutarate [DSG], N,N'-disuccinimidyl carbonate [DSC], dimethyl adipimidate [DMA], dimethyl 3,3-dithiobispropionimidate [DTBP], 4,4'-disiothiocyanatostilbene-2,2'-disulfonic acid salts, 1,5-difluoro-2,4-dinitrobenzene [DFDNB], 4,4'-difluoro-3,3'-dinitrodiphenylsulfone.

Hydroxyl-reactive homobifunctional crosslinking reagents can be used to conjugate a hydroxyl group on a reducing agent or acylated precursor thereof with a hydroxyl group substituent on a chemical or biological T species, a polymer or a surface. Hydroxyl-reactive groups include those having epoxide groups, such as diglycidylethers, particularly 1,4-butanediol diglycidyl ether.

A carboxylate group on a reducing agent or acylated precursor thereof can be conjugated to a carboxylate group substituent on a chemical or biological T species, a polymer or a surface, for example, by generating an active ester at the carboxylate groups and esterifying the active esters with an alkanediol crosslinking reagent, such a 1,6-hexane diol, or 1,12-dodecanediol.

Aldehyde/ketone-reactive homobifunctional crosslinking reagents can be used to conjugate an aldehyde or ketone group of a reducing agent or acylated precursor thereof of this invention with an aldehyde or ketone group substituent on a phenylboronate compound. Bis-hydrazide reagents can be used to crosslink molecules containing aldehyde or ketone groups, examples of such crosslinking reagents include among others adipic acid dihydrazide and carbohydrazide.

Heterobifunctional crosslinking reagents include those which contain an amine reactive group and a sulfhydryl-reactive group. For example, such a heterobifunctional crosslinking reagent can be used to link an amine group on a compound of this invention with a sulfhydryl substituent in a T species of this invention.

Exemplary heterobifunctional crosslinking reagents include those carrying an activated ester group, such as an NHS ester (or sulfo-NHS ester) group or a nitrophenyl or other substituted phenyl ester and a maleimide group; those carrying such an activated ester group and a dithiopyridyl group, those carrying an activated ester group and an haloacetyl group (e.g., an iodoacetyl group), or those carrying an imidoester group and a maleimide group.

Exemplary heterobifunctional amine/sulfhydryl-reactive crosslinking reagents include, among others, N-(y-maleimidobutyryloxy)succinimide ester [GMBS] and its sulfo-NHS analog [sulfo-GMBS], 4-succinimidyloxycarbonyl-α-(2-pyridyldithio)toluene [SMPT], succinimidyl-4-(N-maleimidomethyl)cyclohexane-1-carboxylate [SMCC] and its sulfo-NHS analog [sulfo-SMCC], m-maleimidobenzoyl-N-hydroxysuccinimide ester [MBS] and its sulfo-HNS analog [sulfo-MBS], N-succinimidyl(4-iodoacetyl)-aminobenzoate [SIAB] and its sulfo-HNS analog [sulfo-SIAB], succinimidyl-6-(iodoacetyl)aminohexanoate [SIAX], N-succinimidyl-3-92-pyridylthio)propionate [SPDP], succinimidyl-4-(p-maleimidophenyl)butyrate [SMPB] and its sulfo-NHS analog [sulfo-SMPB], succinimidyl-([N-maleimidopropionamidol]ethyleneglycol esters [SM(PEG)n, where n is 4, 6, 8, 12, 24] and p-nitrophenyl iodoacetate [NPIA], N-hydroxysuccinimidyl 2,3-dibromopropionate [SDBP].

Heterobifunctional crosslinking reagents also include those which contain one of an amine-reactive, carboxylate-reactive or carbonyl-reactive group and a photoreactive group which is activated on irradiation to reactive with various reactive groups, including nucleophiles, reactive hydrogen, active hydrogen amines or olefins.

It will be appreciated that it may be necessary dependent upon the conjugation method employed to acylate or otherwise protect the sulfhydryl groups of the reducing agent or other potentially reactive groups therein from undesired conjugation. Useful thiol protective groups, amine protecting groups and protective groups for various other reactive groups are known in the art, for example as described in Wutts, P. G. and Greene, T. (2007) Green's Protecting Groups in Organic Synthesis (Fourth Edition) John Wiley & Sons, N.Y.

The compounds of formulas I or II can be in the form of salts, for example ammonium (—NR$_6$R$_7$H$^+$) salts, with a selected anion or quaternized ammonium salts (e.g., —NR$_6$R$_7$R$_{20}$$^+$, where R$_{20}$ is a C1-C3 alkyl group). The salts can be formed as is known in the art by addition of an acid to the free base. Salts can be formed with inorganic acids such as hydrochloric acid, hydrobromic acid, sulfuric acid, nitric acid, phosphoric acid and the like, or organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like.

In specific embodiments, compounds of the invention can contain one or more negatively charged groups (free acids) which may be in the form of salts. Exemplary salts of free acids are formed with inorganic base include, but are not limited to, alkali metal salts (e.g., Li$^+$, Na$^+$, K$^+$), alkaline earth metal salts (e.g., Ca$^{2+}$, Mg$^{2+}$), non-toxic heavy metal salts and ammonium (NH$_4$+) and substituted ammonium (N(R')4+ salts, where R' is hydrogen, alkyl, or substituted alkyl, i.e., including, methyl, ethyl, or hydroxyethyl, specifically, tri methyl ammonium, triethyl ammonium, and triethanol ammonium salts), salts of cationic forms of lysine, arginine, N-ethylpiperidine, piperidine, and the like. Compounds of the invention can also be present in the form of zwitterions.

Compounds of formulas I and II also include those which are pharmaceutically acceptable salts, which refers to those salts which retain the biological effectiveness and properties of the free bases or free acids, and which are not biologically or otherwise undesirable.

The scope of the invention as described and claimed encompasses the racemic forms of the compounds as well as the individual enantiomers and non-racemic mixtures thereof. The compounds of the invention may contain one or more asymmetric carbon atoms, so that the compounds can exist in different stereoisomeric forms. The compounds can be, for example, racemates or optically active forms. The optically active forms can be obtained by resolution of the racemates or by asymmetric synthesis. In a preferred embodiment of the invention, enantiomers of the invention exhibit specific rotation that is +(positive). Preferably, the (+) enantiomers are substantially free of the corresponding (−) enantiomer. Thus, an enantiomer substantially free of the corresponding enantiomer refers to a compound which is isolated or separated via separation techniques or prepared free of the corresponding enantiomer. "Substantially free," means that the compound is made up of a significantly greater proportion of one enantiomer. In preferred embodiments the compound is made up of at least about 90% by weight of a preferred enantiomer. In other embodiments of the invention, the compound is made up of at least about 99% by weight of a preferred enantiomer. Preferred enantiomers may be isolated from racemic mixtures by any method known to those skilled in the art, including high performance liquid chromatography (HPLC) and the formation and crystallization of chiral salts or prepared by methods described herein. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, N.Y., 1962); Wilen, S. H. Tables of Resolving Agents and Optical Resolutions p. 268 (E. L. Eliel, Ed., Univ. of Notre Dame Press, Notre Dame, Ind. 1972).

The invention provides methods for reducing or preventing disulfide bond formation in one or more molecules having one or more sulfhydryl groups which comprise the step of contacting the one or more molecules with one or more compounds of this invention, particularly one or more compounds of formula I. In a specific embodiment, the methods are carried out under physiological conditions. In a specific embodiment, the methods are carried out at a pH ranging from 6-8. In a specific embodiment, the methods are carried out at a pH ranging from 6.5 to 7.5. In a specific embodiment, the methods are carried out employing one or more compounds of the invention which are covalently attached to a surface. In specific embodiments, the surface is organic or inorganic with specific examples of such surfaces provided herein. In a specific embodiment, the one or more compounds are S-acylated and the acyl groups are removed to activate the one or more compounds as reducing agents. Activation of the S-acylated compounds can occur prior to contacting the one or more molecules carrying sulfhydryl groups. Activation of the S-acylated compounds can occur at about the same time as contacting the one or more molecules carrying sulfhydryl groups. For example, the contacting step and S-acyl group removal can occur in tissue or in a cell which contains one or more esterases which function for removal of the acyl groups.

In a specific embodiment, reducing or preventing disulfide bond formation reduces or prevents the formation of dimers or other oligomers of the one or more molecules having sulfhydryl groups. In a specific embodiment, reducing or preventing disulfide bond formation functions to modulate a biological activity of the one or more molecules having sulfhydryl groups. Modulation of the biological activity includes a reduction in such activity or an enhancement of such activity. In specific embodiments, the one or more molecules carrying sulfhydryl groups are biological molecules, more specifically are biological macromolecules and yet more specifically are peptides, proteins, carbohydrates or nucleic acids.

In a specific embodiment, the molecules having one or more sulfhydryl groups are peptides or proteins and reducing or preventing disulfide bond formation functions to modulate a biological activity of the one or more peptides or proteins. In a specific embodiment, reducing or preventing disulfide bond formation functions to reduce a biological activity of a peptide or protein. In another embodiment, reducing or preventing disulfide bond formation functions to enhance a biological activity of a peptide or protein. In a specific embodiment, the peptide or protein is redox-sensitive peptide or protein, for example a peptide or proteins the biological activity of which is affected by oxidative stress as is described in Cumming et al. [44]. Cumming et al. is incorporated by reference herein for its description of such redox-sensitive peptides and proteins and specific examples given therein.

Of particular interest for therapeutic application of the compounds of this invention are redox-sensitive peptides and proteins whose function is associated with human or animal disease. Non-limiting specific examples of such redox-sensitive peptides or proteins include PTEN (human phosphatase PTEN), SOD (superoxide dismutase), and pMK2 (an isoform of pyruvate kinase). Decreased PTEN activity is associated with many cancers (i.e., PTEN activity is associated with cancer protection). A cysteine residue near the active site of human phosphatase PTEN is known to be sensitive to oxidation, such that its activity is decreases. Prevention of this inactivation employing a reducing agent or precursor thereof of this invention can be of therapeutic benefit. Superoxide dismutase (Cu/Zn SOD) can be inactivated by the formation of disulfide-linked dimers. Decreased SOD activity is believed to be a cause of amylotropic lateral sclerosis (ALS) [45, 46]. Prevention of decreased SOD activity employing a reducing agent or precursor thereof of this invention can be of therapeutic benefit.

In specific embodiments herein, the dithiol reducing agent, dithiane precursor or acylated precursor thereof is conjugated to a biological or chemical species which targets or directs the conjugated reducing agent to a specific redox-sensitive peptide or protein. The biological or chemical species is for example a ligand, a substrate or a pharmacophore of the target peptide or protein (which may be an enzyme).

PTEN is believed to function by attack/removal of a phosphoryl group from C3 of the inositide below by a cysteine residue. This inositide is the product of PTEN catalysis:

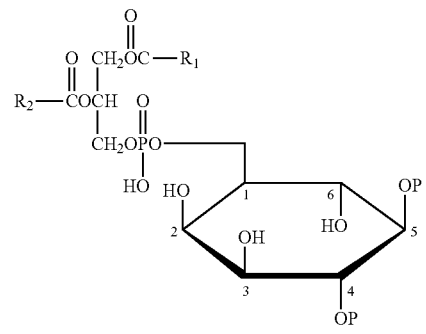

Ptd Ins (4,5)P$_2$

The PTEN cysteine can form a disulfide bond with another cysteine residue inactivating PTEN. This inositide represents a pharmacophore of PTEN and is highly anionic. To target a reducing agent or acylated precursor thereof to PTEN, a highly anionic chemical species can be used which provides a substantial pharmacological equivalent of the phosphoinositol moiety.

A specific example of such a highly anionic chemical species is 1,3,5-tricarboxybenzene. In an exemplary embodiment hereof one or more reducing agents, dithianes or acylated precursors thereof are conjugated to T which is 1,3,5-tricarboxybenzene (or a salt thereof), via one of the carboxyl groups therein:

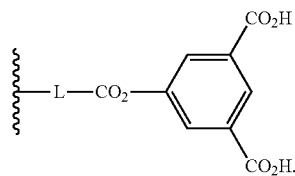

In another exemplary embodiment hereof one or more reducing agents or acylated precursors thereof are conjugated to T which is a 1,3,5-tricarboxybenzyl group (or a salt thereof), via a spacer or linker group:

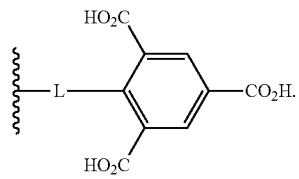

Conjugates of tricarboxybenzene with one or more of the reducing agents of formula I, can be prepared by methods that are well-known in the art, for example by methods that are described in Hermanson, G. T. (2008) Bioconjugate Techniques (Second Edition) Academic Press, N.Y., for example Part I, Chapters 1 and 2. More specifically, a suitable reactive group can be installed on the 1,3,5-tricarboxybenzene and the functionalized T group can then be conjugated to a reducing agent or acylated precursor herein which carries an appropriate reactive group (as described herein above) employing an art-known homo- or heterobifunctional crosslinking reagent as described for example in Hermanson, G. T. (2008) Bioconjugate Techniques (Second Edition) Academic Press, N.Y., Chapters 4 and 5.

More generally the invention provides dithiol reducing agents, dithiane precursors or S-acyl precursors thereof which are targeted to a cationic site for example which contain a pharmacophore of the phosphoinositol moiety.

The invention provides compounds of formulas I and II wherein one of $R_1$ or $R_2$ are:

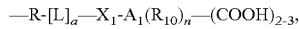

and salts thereof,
where
L is an optional divalent linker as defined above,
$A_1$ is an n-valent di- or tricarboxylic acid species which is selected from an aliphatic group, a heterocyclic group, an aryl group, or a heteroaryl group;
$R_{20}$ is hydrogen, an alkyl group having 1-3 carbon atoms, an aryl group, an arylalkyl group, wherein the alkyl, aryl or aryalkyl group is optionally substituted with one or more halogens, and $X_1$ is a single bond, —O—, —CO—, —OCO—, —NHCO—, —COO—, or —CO—NH—.

In specific embodiments, $A_1$ is a cycloalkyl or cycloalkenyl group having 4-10 carbon atoms. In specific embodiments, $A_1$ is an alkyl group having 5-8 carbon atoms, a phenyl group, a benzyl group, a cyclohexyl group, a cyclohexenyl group, a cyclopentyl group, a cyclobutyl group, a furan, a tetrahydrofuran or a tetrahydropyran. In specific embodiments, the A1 group carries three carboxylic acid groups. In specific embodiments, $X_1$ is a bond. In specific embodiments L is present and is —$(CH_2)_q$—, where q is 0, 1, 2, 3, 4, 5, or 6. In specific embodiments, any $R_{20}$ are hydrogens or alkyl groups having 1-3 carbon atoms. The carboxylic acid substituted $A_1$ group may be a mixture of regioisomers.

Reducing agents and acylated precursors thereof of formulas I are useful as research reagents for reducing disulfide bonds and other redox applications, particularly in applications directed to biological molecules, such as peptide, proteins, carbohydrates and nucleic acids. In various applications, reducing agents of this invention can be added to biological buffers. Compounds of formulas II represent the oxidized form of the reducing agents of formulas I. These oxidized forms are also useful as research reagents, for example, a combination of reduced and oxidized compounds of formulas I and II in appropriate ratio in solution (e.g., aqueous solution) can provide a redox buffer with a selected reduction potential. Redox buffers can be employed for example for refolding of proteins.

One or ordinary skill in the art will recognize additional applications for the reducing agents and acylated precursors thereof. For example, reducing agents are employed for treating hair, e.g. for removal of hair coloring and the like.

The term kit refers to kits including one or more of the reducing agents, or acylated precursors thereof or dithianes precursors thereof which are useful for preventing or inhibiting the formation of disulfide bonds or for cleaving disulfide bonds. In one embodiment, kits of this invention include one or more of the compounds of the present invention or mixtures thereof and optionally reagents for ligating, or conjugating such compounds with a biological or chemical species as discussed herein. The kits optionally include one or more solvents or buffers for application of a reducing agent of this invention. In another embodiment, kits of this invention include one or more compounds of this invention of this invention and optionally reagents, such as one or more homo- or heterobifunctional crosslinking reagents, for ligating or conjugating to a surface. The kit may also include one or more surfaces, for example, in the form of plates, sheets, beads, particles, microspheres, microparticles, nanoparticles or the like to which a compound of this invention is to be immobilized or conjugated. A kit may also include a reagent for removing S-acyl groups of S-acyl precursors of the reducing agents herein, such as hydroxylamine or an esterase.

Kits of the invention may comprise a carrier being compartmentalized to receive in close confinement one or more containers, such as vials, test tubes, ampules, bottles and the like. Each of such container means comprises components or a mixture of components as described above (reducing agents, precursors, solvents or buffers, other reagents, etc.) The kits of the invention may further comprise one or more additional components (e.g., reagents and/or compounds) necessary or desirable for carrying out one or more particular applications of the compositions of the present invention. In general kits may also contain one or more buffers, control samples, carriers or recipients, vessels for carrying out one or more reactions, one or more additional compositions of the invention, one or more sets of instructions, and the like. In specific embodiments of kits herein the reducing agent is BMMP.

The invention is also directed to art-known kits in which DTT therein is replaced with one or more reducing agents of this invention and particularly with BMMP or a salt thereof. Such its include DNA ligation or DNA blunting kits where DTT in buffers therein is replaced with one or more reducing agents of this invention, particularly DTBA or a salt thereof. Kits of this invention also include kits for protein purification or protein assay kits which are compatible with reducing agents.

An aliphatic group as used herein refers to a monovalent non-aromatic hydrocarbon group which include straight chain, branched, or cyclic hydrocarbon groups which can be saturated or unsaturated with one or more double bonds or one or more triple bonds. Aliphatic groups may contain portions which are straight-chain or branched in combination with one or more carbon rings. Carbon rings of aliphatic groups may contain one or more double bonds or one or more triple bonds. Carbon rings of aliphatic groups can contain 3- to 10-membered rings. Such carbon rings may be fused and may be bicyclic or tricyclic. Aliphatic groups are optionally substituted with one or more non-hydrogen substituents where optional substituents are described herein. Unless otherwise specified, an aliphatic group can contain 1-20 carbon atoms or can contain 1-10 carbon atoms. Aliphatic groups include those containing 1-3, 1-6, and 1-8 carbon atoms. Aliphatic groups include, among others, alicyclic groups, alkyl groups, alkenyl groups and alkynyl groups.

An alicyclic group as used herein refers to a monovalent non-aromatic cyclic hydrocarbon group which can be saturated or unsaturated with one or more double bonds or one or more triple bonds. Alicyclic rings include those containing 3- to 10-membered carbon rings. Alicyclic groups include those containing one, two, three or more rings which may be fused or linked by straight chain or branched alkylene, alkenylene or alkynylene moieties. Alicyclic groups include bicyclic and tricyclic rings. Alicyclic groups include those in which one or more carbon rings are substituted with a straight-chain or branched alkyl, alkenyl or alkynyl group. To satisfy valence requirements, a ring atom may be substituted with hydrogen or optionally with non-hydrogen substituents as described herein. One or more carbons in an alicyclic group can be —CO— groups, i.e. a carbon can be substituted with an oxo (=O) moiety. Alicyclic groups are optionally substituted with one or more non-hydrogen substituents where optional substituents are described herein. Unless otherwise specified, an alicyclic group can contain 3-20 carbon atoms or can contain 3-12 carbon atoms. Alicyclic groups include those containing 3-6 and 3-8 carbon atoms. Alicyclic groups include among others cycloalkyl, cycloalkenyl, cyclopropyl, cyclobutyl, cyclopentyl, cyclopentadienyl, cyclohexyl, cyclohexenyl and cyclohexadienyl groups, all of which are optionally substituted.

A heterocyclic group as used herein refers to a monovalent non-aromatic cyclic hydrocarbon group wherein one or more of the rings contain one or more heteroatoms (e.g., N, S, O, or P) which rings can be saturated or unsaturated with one or more double bonds or one or more triple bonds. In specific embodiments of this invention, heterocyclic rings which are substituents of the compounds of formulas IA and IB do not contain boron atoms. Heterocyclic rings include those containing 3- to 10-membered rings where 1, 2 or 3 of the ring members are heteroatoms. Heterocyclic groups include those containing one, two, three or more rings which may be fused or linked by straight chain or branched alkylene, alkenylene or alkynylene moieties. Heterocyclic groups include bicyclic and tricyclic groups. Heterocyclic groups include those in which a heterocyclic ring is substituted with a straight-chain or branched alkyl, alkenyl or alkynyl group. To satisfy valence requirements, a ring atom may be substituted with hydrogen or optionally with non-hydrogen substituents as described herein. One or more carbons in a heterocyclic group can be —CO— groups. One or more carbons in a heterocyclic ring can be —CO-groups. Heterocyclic groups are optionally substituted with one or more non-hydrogen substituents where optional substituents are described herein. Ring carbons and, where chemically feasible, ring heteroatoms are optionally substituted. Unless otherwise specified, a heterocyclic group can contain 3-20 carbon atoms, can contain 3-12 carbon atoms or can contain 3-6 carbon atoms. Heterocyclic groups include those containing one or two 4-, 5- or 6-member rings at least one of which has one, two or three N, O or S atoms and wherein a ring optionally has one or two double bonds. Heterocyclic groups include those containing a single 5- or 6-member ring having one, two or three N, O or S atoms and optionally having one or two double bonds. Heterocyclic groups include those having 5- and 6-member rings with one or two nitrogens and one or two double bonds. Heterocyclic groups include those having 5- and 6-member rings with an oxygen or a sulfur and one or two double bonds. Heterocyclic groups include those having 5- or 6-member rings and two different heteroatom, e.g., N and O, O and S or N and S. Heterocyclic groups include those having 5- or 6-member rings and a single heteroatom, e.g., N S or O. Specific heterocyclic groups include among others among others, pyrrolidinyl, piperidyl, piperazinyl, pyrrolyl, pyrrolinyl, furyl, tetrahydropyranyl, tetrahydrofuryl, thienyl, morpholinyl, oxazolyl, oxazolinyl, oxazolidinyl, indolyl, triazoly, and triazinyl groups, all of which are optionally substituted.

Aryl groups are monovalent groups containing at least one aromatic ring. Aryl groups include groups having one or more 5- or 6-member aromatic rings. Aryl groups can contain one, two or three, 6-member aromatic rings. Aryl groups can contain two or more fused aromatic rings. Aryl groups can contain two or three fused aromatic rings. Aryl groups may contain one or more non-aromatic alicyclic rings in addition to an aromatic ring. Aryl groups are optionally substituted with one or more non-hydrogen substituents as described herein. Substituted aryl groups include among others those which are substituted with alkyl or alkenyl groups, which groups in turn can be optionally substituted. Specific aryl groups include phenyl groups, biphenyl groups, and naphthyl groups, all of which are optionally substituted as described herein. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Unless otherwise specified, an aryl group can contain 5-20 carbon atoms or can contain 6-14 carbon atoms. Aryl groups also include those containing 6-12 carbon atoms.

Heteroaryl groups are monovalent groups having one or more aromatic rings in which at least one ring contains a heteroatom (a non-carbon ring atom). Heteroaryl groups include those having one or two heteroaromatic rings carrying 1, 2 or 3 heteroatoms and optionally having one 6-member aromatic ring. Heteroaryl groups can contain 5-20, 5-12 or 5-10 ring atoms. Heteroaryl groups include those having at least one aromatic ring containing a heteroatom and one or two alicyclic, heterocyclic or aryl ring groups. Heteroaryl groups include those having one aromatic ring containing a heteroatom and one aromatic ring containing carbon ring atoms. Heteroaryl groups include those having one or more 5- or 6-member aromatic heteroaromatic rings and one or more 6-member carbon aromatic rings.

Heteroaromatic rings can include one or more N, O, or S atoms in the ring. Heteroaromatic rings can include those with one, two or three N, those with one or two O, and those with one or two S, or combinations of one or two or three N, O or S. Specific heteroaryl groups include pyridinyl, pyrazinyl, pyrimidinyl, quinolinyl, and purinyl groups.

Alkyl groups are monovalent groups and include straight-chain, branched and cyclic alkyl groups. Unless otherwise indicated alkyl groups include those having from 1 to 20 carbon atoms. Alkyl groups include alkyl groups having 1 to 3 carbon atoms, alkyl groups having from 4-7 carbon atoms and alkyl groups having 8 or more carbon atoms. Cyclic alkyl groups include those having one or more rings. Cyclic alkyl groups include those which have 1, 2 or 3 rings. Cyclic alkyl groups also include those having 3-10 carbon atoms. Cyclic alkyl groups include those having a 3-, 4-, 5-, 6-, 7-, 8-, 9- or 10-member carbon ring and particularly those having a 3-, 4-, 5-, 6-, 7-, or 8-member ring. The carbon rings in cyclic alkyl groups can also carry straight-chain or branched alkyl group substituents. Cyclic alkyl groups can include bicyclic and tricyclic alkyl groups. Alkyl groups are optionally substituted with one or more non-hydrogen substituents as described herein. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, cyclohexyl, decalinyl, and norbornyl, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups. Substituted alkyl group include alkyl group substituted with one or more hydroxyl groups. Substituted alkyl groups include groups substituted with two or more hydroxyl groups, particularly where two hydroxyl groups are substituted on adjacent carbon atoms.

Arylalkyl groups are monovalent alkyl groups substituted with one or more aryl groups wherein the alkyl groups optionally carry additional substituents and the aryl groups are optionally substituted. Specific arylakyl groups are phenyl-substituted alkyl groups, e.g., benzyl groups or phenethyl groups which are optionally substituted. Heteroarylalkyl groups are monovalent alkyl groups substituted with one or more heteroaryl groups wherein the alkyl groups optionally carry additional substituents and the aryl groups are optionally substituted. Alkylaryl groups are monovalent aryl groups substituted with one or more alkyl groups wherein the alkyl groups optionally carry additional substituents and the aryl groups are further optionally substituted. Specific alkylaryl groups are alkyl-substituted phenyl groups such as o-, m- or p-tolyl groups which are optionally substituted. Alkylheteroaryl groups are monovalent alkyl groups substituted with one or more heteroaryl groups wherein the alkyl groups optionally carry additional substituents and the heteroaryl groups are optionally substituted.

Alkenyl groups include monovalent straight-chain, branched and cyclic alkenyl groups which contain one or more carbon-carbon double bonds. Unless otherwise indicated alkenyl groups include those having from 2 to 20 carbon atoms. Alkenyl groups include those having 2 to 4 carbon atoms and those having from 5-8 carbon atoms. Cyclic alkenyl groups include those having one or more rings wherein at least one ring contains a double bond. Cyclic alkenyl groups include those which have 1, 2 or 3 rings wherein at least one ring contains a double bond. Cyclic alkenyl groups also include those having 3-10 carbon atoms. Cyclic alkenyl groups include those having a 5-, 6-, 7-, 8-, 9- or 10-member carbon ring and particularly those having a 5- or 6-member ring. The carbon rings in cyclic alkenyl groups can also carry straight-chain or branched alkyl or alkenyl group substituents. Cyclic alkenyl groups can include bicyclic and tricyclic alkyl groups wherein at least one ring contains a double bond. Alkenyl groups are optionally substituted with one or more non-hydrogen substituents as described herein. Specific alkenyl groups include ethylene, propenyl, cyclopropenyl, butenyl, cyclobutenyl, pentenyl, pentadienyl, cyclopentenyl, cyclopentadienyl, hexylenyl, hexadienyl, cyclohexenyl, cyclohexadienyl, including all isomers thereof and all of which are optionally substituted. Substituted alkenyl groups include fully halogenated or semihalogenated alkenyl groups.

Alkynyl groups include mono-valent straight-chain, branched and cyclic alkynyl group which contain one or more carbon-carbon triple bonds. Unless otherwise indicated alkynyl groups include those having from 2 to 20 carbon atoms. Alkynyl groups include those having 2 to 4 carbon atoms and those having from 5-8 carbon atoms. Cyclic alkynyl groups include those having one or more rings wherein at least one ring contains a triple bond. Cyclic alkynyl groups include those which have 1, 2 or 3 rings wherein at least one ring contains a triple bond. Cyclic alkynyl groups also include those having 3-10 carbon atoms. Cyclic alkynyl groups include those having a 5-, 6-, 7-, 8-, 9- or 10-member carbon ring and particularly those having a 5- or 6-member ring.

The carbon rings in cyclic alkynyl groups can also carry straight-chain or branched alkyl, alkenyl or alkynyl group substituents. Cyclic alkynyl groups can include bicyclic and tricyclic alkyl groups wherein at least one ring contains a triple bond. Alkynyl groups are optionally substituted with one or more non-hydrogen substituents as described herein.

An alkoxy group is an alkyl group (including cycloalkyl), as broadly discussed above, linked to oxygen, a monovalent —O-alkyl group. An aryloxy group is an aryl group, as discussed above, linked to an oxygen, a monovalent —O-aryl. A heteroaryloxy group is a heteroaryl group as discussed above linked to an oxygen, a monovalent —O-heteroaryl. Alkenoxy, alkynoxy, alicycloxy, heterocycloxy groups are analogously defined. All of such groups are optionally substituted.

An alkoxyalkyl group as used herein refers generally and formally to an alkyl group wherein one or more —$CH_2$— groups therein are replaced with —O—. An alkoxyalkyl group includes groups which are bonded to a chemical species by carbon-oxygen bonds or by carbon-carbon bonds. Alkoxyalkyl groups, unless otherwise specified, can contain 2-20 carbon atoms and 1-10 oxygen atoms. Exemplary alkoxyalkyl groups include among others: —[($CH_2$)$y_a$-O]$_a$—$R_A$ or —O—[($CH_2$)$y_a$-O]$_a$—$R_A$, where $R_A$ is an alkyl group, a is an integer from 1-10, preferably 1-5 and each $y_a$ is the same or different and is an integer from 1-6, preferably 2-4. One or more carbons of the alkoxyalkyl group is optionally substituted, particularly with one or more alkyl or alkoxyl groups having 1-3 carbon atoms.

An acyl group has the formula $R_{AC}$CO—, where $R_{AC}$ is an alkyl, alkenyl, alkynyl, aryl, heteroaryl, or heterocyclic group, each of which is optionally substituted. In specific embodiments, the acyl group is an alkylacyl group where $R_{AC}$ is an alkyl group as described above. More specifically $R_{AC}$ is an alkyl group having 1-6 or 1-3 carbon atoms. A specific acyl group is an acetyl group ($CH_3$—CO—). In a specific embodiment, $R_{AC}$ is an aryl substituted alkyl group, such as a benzyl group ($C_6H_6$—$CH_2$—) or phenethyl group ($C_6H_6$—$CH_2$—$CH_2$—)—, the phenyl rings of which are optionally substituted. In a specific embodiment, $R_{AC}$ is an aryl group, specifically a phenyl group, particularly optionally substituted phenyl groups.

As to any of the chemical groups herein which contain one or more substituents, it is understood, that such groups do not contain any substitution or substitution patterns which are sterically impractical and/or synthetically non-feasible. In addition, the compounds of this invention include all stereochemical isomers arising from the substitution of these compounds. Optionally substituted chemical groups herein can carry one or more non-hydrogen substituents. In specific embodiments, optionally substituted chemical groups carry one non-hydrogen substituent. In specific embodiments, optionally substituted chemical groups carry two non-hydrogen substituent. In specific embodiments, optionally substituted chemical groups carry three non-hydrogen substituent.

The dithiol of this invention as illustrated in formulas I and their oxidized forms as in formula II are prepared in view of the descriptions herein, what is known in the art or by routine adaptation of art-known methods from starting materials and reagents which are commercially available or which can be prepared by methods that known in the art or routine adaptation of such methods. An exemplary method is provided in the Examples.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. A number of specific groups of variable definitions have been described herein. It is intended that all combinations and subcombinations of the specific groups of variable definitions are individually included in this disclosure. Compounds described herein may exist in one or more isomeric forms, e.g., structural or optical isomers. When a compound is described herein such that a particular isomer, enantiomer or diastereomer of the compound is not specified, for example, in a formula or in a chemical name, that description is intended to include each isomers and enantiomer (e.g., cis/trans isomers, R/S enantiomers) of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Isotopic variants, including those carrying radioisotopes, may also be useful in diagnostic assays and in therapeutics. Methods for making such isotopic variants are known in the art. Specific names of compounds are intended to be exemplary, as it is known that one of ordinary skill in the art can name the same compounds differently. Molecules disclosed herein may contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Compounds of the invention, and salts thereof, may exist in their tautomeric form, in which hydrogen atoms are transposed to other parts of the molecules and the chemical bonds between the atoms of the molecules are consequently rearranged. It should be understood that all tautomeric forms, that may exist, are included within the invention.

Every formulation or combination of components described or exemplified herein can be used to practice the invention, unless otherwise stated.

Whenever a range is given in the specification, for example, a temperature range, a pH range, a time range, or a composition or concentration range, the range is inclusive and all intermediate ranges and subranges, as well as all individual values included in the ranges given are intended to be included in the disclosure. It is to be understood that any subranges or individual values in a range or subrange that are included in the description herein can be excluded from the claims herein.

All references throughout this application, for example patent documents including issued or granted patents or equivalents; patent application publications; and non-patent literature documents or other source material; are hereby incorporated by reference herein in their entireties, as though individually incorporated by reference.

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. The broad term comprising is intended to encompass the narrower consisting essentially of and the even narrower consisting of. Thus, in any recitation herein of a phrase "comprising one or more claim element" (e.g., "comprising A and B"), the phrase is intended to encompass the narrower, for example, "consisting essentially of A and B" and "consisting of A and B." Thus, the broader word "comprising" is intended to provide specific support in each use herein for either "consisting essentially of" or "consisting of." The invention illustratively described herein suitably may be practiced in the absence of any element or elements, limitation or limitations which is not specifically disclosed herein.

One of ordinary skill in the art will appreciate that starting materials, catalysts, reagents, synthetic methods, purification methods, analytical methods, and assay methods, other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by examples, preferred embodiments and optional features, modification and variation of the concepts herein disclosed may be resorted to by those skilled in the art, and that such modifications and variations are considered to be within the scope of this invention as defined by the appended claims.

All references cited herein are hereby incorporated by reference to the extent that there is no inconsistency with the disclosure of this specification. Some references provided herein are incorporated by reference to provide details concerning sources of starting materials; alternative starting materials, reagents, methods of synthesis, purification methods, and methods of analysis; as well as additional uses of the invention.

The following examples are intended to be illustrative of the invention and not intended to limit the invention.

THE EXAMPLES

Example 1

Commercial reagents were used without further purification. Dithiothreitol (DTT) was from Research Products International (Mt. Prospect, Ill.). Papain (lyophilized powder from *papaya* latex), creatine kinase (lyophilized powder from rabbit muscle), hexokinase (lyophilized powder from *Saccharomyces cerevisiae*), glucose-6-phosphate dehydrogenase (ammonium sulfate suspension from baker's yeast), $N_\alpha$-benzoyl-L-arginine-4-nitroanilide hydrochloride, S-methyl methanethiosulfonate, trans-4,5-di hydroxy-1,2-dithiane (oxidized DTT), 2-mercaptoethanol, oxidized 2-mercaptoethanol, and 2-butyne-1,4-diol were from Sigma-Aldrich (St. Louis, Mo.). DTBA and oxidized DTBA were synthesized as described previously. [23]

All glassware was oven or flame-dried, and reactions were performed under $N_2$(g) unless stated otherwise. Dichloromethane was dried over a column of alumina. Triethylamine and dimethylformamide (DMF) were dried over a column of alumina and purified further by passage through an isocyanate scrubbing column. Flash chromatography was performed with columns of 40-63 Å silica, 230-400 mesh (Silicycle, Québec City, Canada). Thin-layer chromatography (TLC) was performed on plates of EMD 250-um silica 60-$F_{254}$.

The term "concentrated under reduced pressure" refers to the removal of solvents and other volatile materials using a rotary evaporator at water-aspirator pressure (<20 torr) while maintaining the water-bath temperature below 40° C. Residual solvent was removed from samples at high vacuum (<0.1 torr). The term "high vacuum" refers to vacuum achieved by a mechanical belt-drive oil pump.

Analytical samples of BMMP and BMMP$^{ox}$ were obtained using a Shimadzu (Kyoto, Japan) preparative HPLC, equipped with a C18 reverse-phase preparative column, Prominence diode array detector, and fraction collector. Ellman's assay for sulfhydryl groups was performed using a Varian Cary 60 Bio UV-Vis spectrophotometer. Equilibrium, reduction potential, and kinetic studies on small molecules were performed with an analytical HPLC (Waters system equipped with a Waters 996 photodiode array detector, Empower 2 software and a Varian C18 reverse-phase column).

Thiol $pK_a$ values were determined using a Varian Cary 60 UV-Vis spectrophotometer. Kinetic studies on proteins were carried out using a Varian Cary 400 Bio UV-Vis spectrometer with a Cary temperature controller at the Biophysics Instrumentation Facility at Madison (BIF). All NMR spectra were acquired at ambient temperature with a Bruker DMX-400 Avance spectrometer and a Bruker Avance III 500ii with cyroprobe spectrometer at the National Magnetic Resonance Facility at Madison (NMRFAM), and were referenced to TMS or residual protic solvent.

Example 2

Exemplary Chemical synthesis

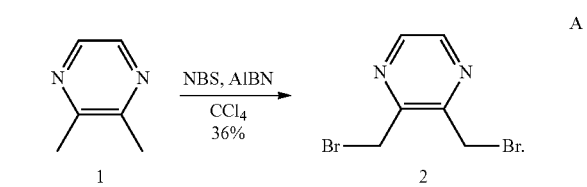

Compound 2 was synthesized as described previously from 2,3-dimethylpyrazine (1) resulting in comparable yields and identical NMR spectra [37].

$^1$H NMR (400 MHz, CDCl$_3$) δ=8.43 (s, 2H), 4.65 (s, 4H); $^{13}$C NMR (125 MHz, CDCl$_3$)=151.4, 143.9, 29.5.

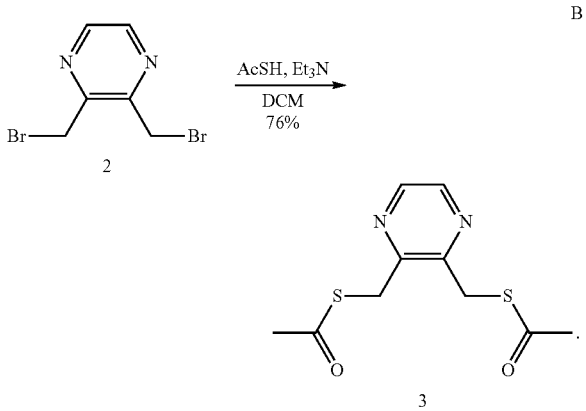

A flame-dried round-bottom flask was charged with 2 (0.907 g, 3.411 mmol), dissolved with 35 mL of dichloromethane, and placed under an atmosphere of dry $N_2$(g). Triethylamine (1.50 mL, 10.76 mmol) and thioacetic acid (AcSH, 0.54 mL, 7.56 mmol) were then added, and the resulting solution was stirred overnight. After 16 h, the reaction was concentrated under reduced pressure and the resulting residue was purified by column chromatography (40% v/v ethyl acetate in hexanes) resulting in 3 (0.664 g, 76%).

$^1$H NMR (400 MHz, CDCl3) δ5=8.42 (s, 2H), 4.43 (s, 4H), 2.39 (s, 6H); 13C NMR (100 MHz, CDCl$_3$) δ=194.4, 151.1, 142.8, 32.4, 30.2; HRMS (ESI) calculated for $[C_{10}H_{13}N_2O_2S_2]^+$ (M+H+) requires m/z=257.0413, found 257.0422.

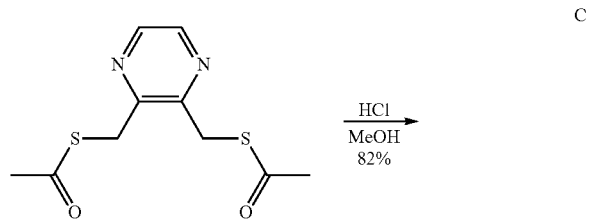

To a flame-dried flask containing 3 (0.167 g, 0.651 mmol) was added 6 mL of anhydrous MeOH followed by 3 mL of 3N HCl in MeOH. After reacting for 16 h under $N_2(g)$, the reaction mixture was concentrated under reduced pressure, passed through a 4.5-μm filter, and purified by reverse-phase HPLC using a preparatory C18 column and a linear gradient of 10-80% v/v acetonitrile (0.1% v/v TFA) in water (0.1% v/v TFA) over 45 min. BMMP (4) eluted at 27 min and, after lyophilization, was isolated as an off white/yellow powder (91.9 mg, 82%).

$^1$H NMR (400 MHz, DMSO-d$_6$) δ=8.46 (s, 2H), 3.97 (d, J=7.5 Hz, 4H), 3.05 (t, J=7.5 Hz, 2H); NMR (100 MHz, DMSO-d$_6$) δ=153.3, 142.5, 26.8; HRMS (EI) calculated for $[C_6H_8N_2S_2]^+$ (M$^+$) requires m/z=127.0124, found 172.0125.

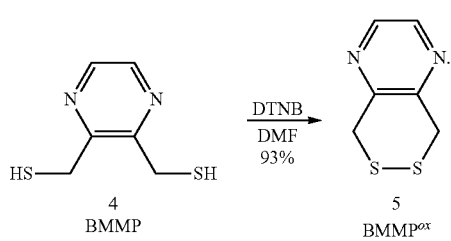

BMMP 4 (51.5 mg, 0.299 mmol) and 5,5'-dithio-bis(2-nitrobenzoic acid) (DTNB, 118.9 mg, 0.300 mmol) were placed in a 25-mL round-bottom flask. These solids were dissolved in 7 mL of anhydrous DMF, and the reaction mixture was stirred under $N_2(g)$. After 24 h, the solvent was removed by rotary evaporation under high vacuum, passed through a 4.5-μm filter, and purified by reverse-phase HPLC using a preparatory C18 column and a linear gradient of 10-80% v/v acetonitrile (0.1% v/v TFA) in water (0.1% v/v TFA) over 45 min. BMMP$^{ox}$ (5) eluted at 36 min, and after lyophilization, was isolated as an off white/yellow powder (47.3 mg, 93%).

$^1$H NMR (400 MHz, CDCl$_3$) δ=8.42 (s, 2H), 4.25 (s, 4H); NMR (100 MHz, CDCl$_3$) δ=149.8, 142.2, 37.9; HRMS (EI) calculated for $[C_6H_6N_2S_2]^+$ (M$^+$) requires m/z=169.9967, found 169.9961.

Example 3

Determination of Thiol $pK_a$ Values

The thiol $pK_a$ values are determined by following a procedure reported previously that exploits the elevated absorbance of the deprotonated thiolate at 238 nm. [27, 28, 23] A plot of $A_{238}$ vs pH was recorded (FIGS. 4A and 4B), and $pK_a$ values were determined by fitting these data to eq 1, which is derived from Beer's law and the definition of the acid dissociation constant [38].

$$A_{238} = C_T\left(\frac{\varepsilon_{S^-}^{S^-}10^{(pH-pKa2)} + \varepsilon_{SH}^{S^-} + \varepsilon_{SH}^{SH}10^{(pKa1-pH)}}{10^{(pH-pKa2)} + 1 + 10^{(pKa1-pH)}}\right) \quad (1)$$

Figure 4A:
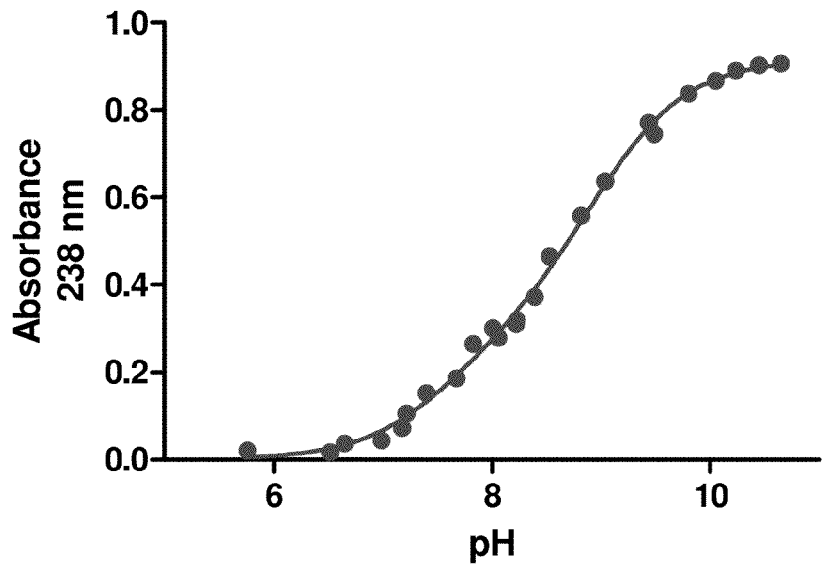
FIGS. 4A and 4B are graphs of the effect of pH on absorbance by (A) BMMP at 238 nm in a 0.10 M potassium phosphate buffer. $pK_a$ values of 7.6±0.1 and 9.0±0.1, and extinction coefficients of $\epsilon_{SH}^{SH}$=5.24, $\epsilon_{SH}^{S-}$=3058, $\epsilon_{S-}^{S-}$=9159 M$^{-1}$cm$^{-1}$ with $r^2$>0.99 were determined by fitting the data to eq 1; and (B) DMH at 238 nm in a 0.10 M potassium phosphate buffer. $pK_a$ values of 8.0±0.2 and 9.1±0.1, and extinction coefficients of $\epsilon_{SH}^{SH}$=67.8, $\epsilon_{SH}^{S-}$=3885, $\epsilon_{S-}^{S-}$=9116 M$^{-1}$cm$^{-1}$ with $r^2$>0.99 were determined by fitting the data to eq 1.

For BMMP determination, in eq 1, $C_T$ is the total thiol concentration, $\varepsilon_{SH}^{SH}$ is the extinction coefficient of the doubly protonated form of BMMP, $\varepsilon_{SH}^{S^-}$ is the extinction coefficient of the singly protonated form of BMMP, and $\varepsilon_{S^-}^{S^-}$ is the extinction coefficient of the doubly deprotonated form of BMMP. FIG. 4A illustrates the effect of pH on absorbance by BMMP at 238 nm in a 0.10 M potassium phosphate buffer. $pK_a$ values of 7.6±0.1 and 9.0±0.1, and extinction coefficients of $\varepsilon_{SH}^{SH}$=5.24, $\varepsilon_{SH}^{S^-}$=3058, $\varepsilon_{S^-}^{S^-}$=9159 M$^{-1}$cm$^{-1}$ with $r^2$>0.99 were determined by fitting the data to eq 1.

Figure 4B:
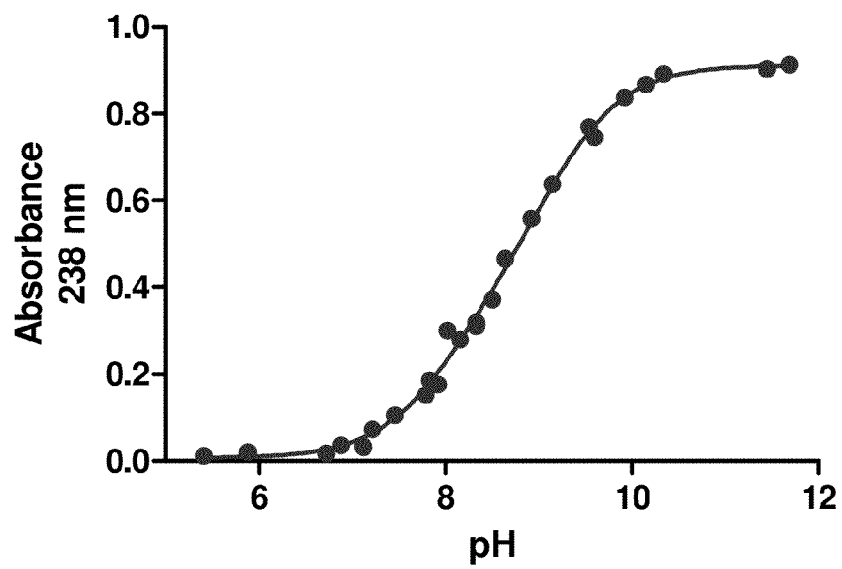

For comparison, the thiol $pK_a$ values for DMH were determined in a similar fashion. FIG. 4B illustrates the effect of pH on absorbance by DMH at 238 nm in a 0.10 M potassium phosphate buffer. $pK_a$ values of 8.0±0.2 and 9.1±0.1, and extinction coefficients of $\varepsilon_{SH}^{SH}$=67.8, $\varepsilon_{SH}^{S^-}$=3885, $\varepsilon_{S^-}^{S^-}$=9116 M$^{-1}$cm$^{-1}$ with $r^2$>0.99 were determined by fitting the data to eq 1.

Reduction Potential of BMMP

Following a procedure reported previously [9, 23] the reduction potential of BMMP was determined by analyzing its equilibrium reaction with DTTox (eq 2), and measuring the amount of reduced and oxidized species in solution by analytical HPLC. Once the equilibrium constant was determined, its value was plugged into a variation of the Nernst equation (eq 3). 5 BMMP (2.5 mg, 0.015 mmol) and DTTox (2.3 mg, 0.015 mmol) were place in a 10 mL round-bottom flask, and 5 mL of degassed 50 mM potassium phosphate buffer, pH 7.0, containing EDTA (2 mM) was added. The reaction mixture was then sonicated briefly to ensure complete dissolution of material and stirred overnight under $N_2(g)$. After reacting for 24 h, the reaction mixture was quenched by the addition of 0.1 mL of 3 N HCl, and passed through a 4.50-μm filter. A 100-μL aliquot of the reaction mixture was then immediately analyzed by analytical HPLC using a Waters system equipped with a Waters 996 photodiode array detector, Empower 2 software, and a Varian C18 column. The column was eluted at 1.0 mL/min with water (5.0 mL), followed by a linear gradient (0-40% v/v) of acetonitrile/water over 40 min. Four peaks were observed, corresponding to DTT (18 min), DTTox (22 min), BMMP (34 min), and BMMPox (41 min). Calibration curves were generated and found to be linear over the concentration range analyzed. From these curves, equilibrium concentrations were determined, and a Keq=0.137±0.036 was determined for the reaction. Next, using this value and assuming $E^\sigma = -0.327$ V for DTT, a variation of the Nernst equation (eq 3) was used to calculate that BMMP has a reduction potential of $E^\sigma = (-0.301 \pm 0.003)$ V. This value is the mean±SE from three separate experiments.

$$K_{eq} = \frac{[DTT][\text{oxidized } BMMP]}{[BMMP][\text{oxidized } DTT]} \quad (2)$$

$$E'^{o}_{BMMP} = E'^{o}_{DTT} - \frac{RT}{nF}\ln\frac{[DTT][\text{oxidized } BMMP]}{[BMMP][\text{oxidized } DTT]} \quad (3)$$

For comparison, the reduction potential of DMH was also determined by following the same procedure. With $K_{eq}=0.0065\pm0.0020$ and assuming $E^\sigma = -0.327$ V for DTT, DMH was found to have $E^\sigma = (-0.262 \pm 0.004)$ V.

Equilibrium Reaction with Oxidized βME

First, 4.0 mL of freshly degassed 50 mM potassium phosphate buffer, pH 7.0, containing EDTA (2 mM) was added to a round-bottom flask containing 3.0 mg (0.017 mmol) of BMMP. The flask was briefly sonicated to ensure complete dissolution of material and then stirred on under $N_2(g)$. Next, 0.6 mL (0.006 mmol) of a 10 mM stock solution of βMEox was added and the reaction was stirred overnight. After 24 h, the reaction mixture was quenched by the addition of 0.1 mL of 3 N HCl, filtered through a 4.5-μm solution, and immediately analyzed by analytical HPLC using a Waters system equipped with a Waters 996 photodiode array detector, Empower 2 software, and a Varian C18 column. The column was eluted at 1.0 mL/min with water (5.0 mL), followed by a linear gradient (0-40% v/v) of acetonitrile/water over 40 min. Three peaks were observed, corresponding to βME (6 min), BMMP (34 min), and BMMPox (41 min). The peak corresponding to βMEox (21 min) was not observed, indicative of the quantitative reduction of βMEox to form βME. This experiment was repeated three times with identical results.

Reduction Kinetics on Oxidized βME $$-\frac{\partial [\text{disulfide}]_{total}}{\partial t} = k_{obs}[\text{disulfide}]_{total}[\text{thiol}]_{total}$$

Figure 1:
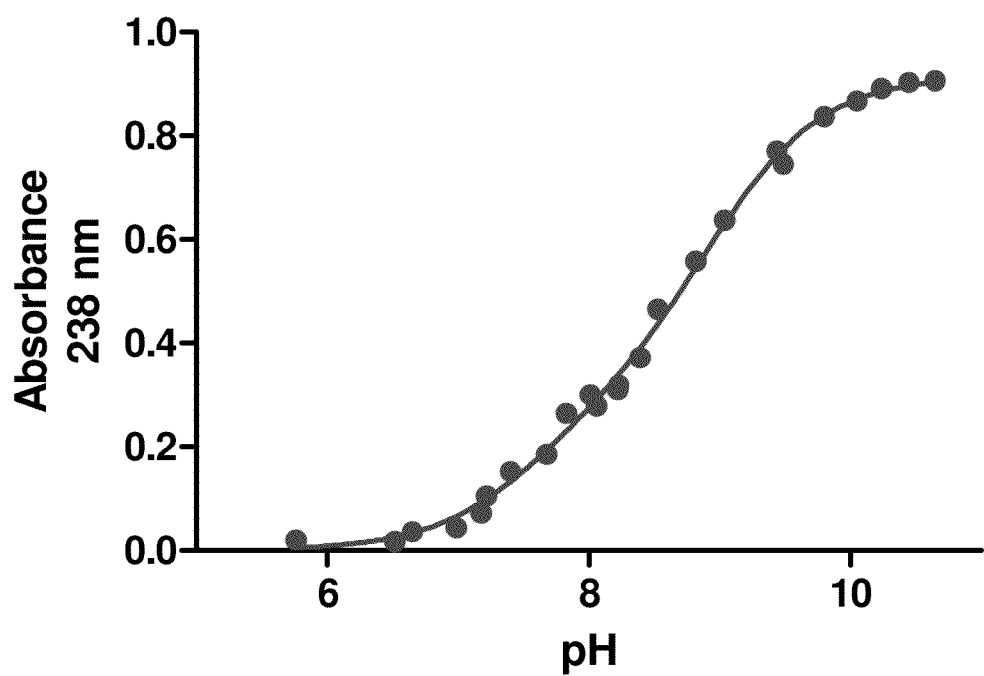
FIG. 1 is a graph showing the effect of pH on absorbance by BMMP at 238 nm in a 0.10 M potassium phosphate buffer. pKa values of 7.6±0.1 and 9.0±0.1, and extinction coefficients of $\epsilon_{SH}^{SH}$=5.24, $\epsilon_{SH}^{S-}$=3058, $\epsilon_{S-}^{S-}$=9159 M-1 cm-1 with $r^2$>0.99 were determined by fitting the data to eq 1.

The observed second-order rate constant ($k_{obs}$) for the reduction oxidized βME by BMMP, DTBA, and DTT was determined by following a previously described procedure [21, 23]. A 10 mL round-bottom flask was charged with BMMP (4.3 mg, 0.025 mmol), DTBA (4.3, 0.025 mmol), or DTT (3.9 mg, 0.025 mmol). Under an atmosphere of $N_2(g)$, 2.5 mL of freshly degassed 50 mM potassium phosphate buffer, pH 7.0, was then added to the reaction flask and the solution was briefly sonicated to ensure complete dissolution of reducing agent. At time t=0, 2.5 mL of a 10 mM stock solution of $\beta ME^{ox}$ in 50 mM potassium phosphate buffer, pH 7.0, was then added. At various time points (1, 2, and 4 min), the reaction mixture was quenched by the addition of 0.1 mL of 3 N HCl. The reaction mixture was then passed through a 4.5-μm filter and analyzed immediately by analytical HPLC using a Varian C18 reverse-phase column. The mixture was eluted at 1.0 mL/min with water (5.0 mL), followed by a linear gradient (0-40% v/v) of acetonitrile/water over 40 min. The degree of reduction was determined by integrating the newly formed peak in the chromatogram corresponding to reduced βME (elution time of 6 min) at 205 nm. Calibration curves were generated and determined to be linear over the concentration range. The amount of residual oxidized BME was calculated, and the second-order rate constants were determined from the linear fit of the data in FIG. 1A ($k_{obs}= [(1/C_{final})-(1/C_{initial})]/t$). The initial values of concentration ($C_{initial}$) were: BMMP (or DTBA or DTT)=$\beta ME^{ox}$=5 mM. Rate constants were the mean±SE from three independent experiments: BMMP, $k_{obs}$=(1.02±0.07) $M^{-1}s^{-1}$; DTBA, $k_{obs}$=(0.32±0.02) $M^{-1}s^{-1}$; and DTT, $k_{obs}$=(0.090±0.005) $M^{-1}s^{-1}$. The same procedure was repeated 50 mM sodium acetate buffer, pH 5.0, yielding rate constants: BMMP, $k_{obs}$=(0.0183±0.0007) $M^{-1}s^{-1}$; DTBA, $k_{obs}$=(0.0051±0.0004) $M^{-1}s^{-1}$; and DTT: $k_{obs}$=(0.0013±0.0001) $M^{-1}s^{-1}$.

Reduction Kinetics on Oxidized βME $$-\frac{\partial [\text{disulfide}]_{total}}{\partial t} = k_{obs}[\text{disulfide}]_{total}[\text{thiol}]_{total}$$

The observed second-order rate constant ($k_{obs}$) for the reduction oxidized βME by BMMP, DMH, DTBA, and DTT was determined by following a previously described procedure.[1,4] A 10 mL round-bottom flask was charged with BMMP (4.3 mg, 0.025 mmol), DTBA (4.3, 0.025 mmol), or DTT (3.9 mg, 0.025 mmol). Under an atmosphere of $N_2(g)$, 2.5 mL of freshly degassed 50 mM potassium phosphate buffer, pH 7.0, was then added to the reaction flask and the solution was briefly sonicated to ensure complete dissolution of reducing agent. At time t=0, 2.5 mL of a 10 mM stock solution of $\beta ME^{ox}$ in 50 mM potassium phosphate buffer, pH 7.0, was then added. At various time points (1, 2, and 4 min), the reaction mixture was quenched by the addition of 0.1 mL of 3 N HCl. The reaction mixture was then passed through a 4.5-μm filter and analyzed immediately by analytical HPLC using a Varian C18 reverse-phase column. The mixture was eluted at 1.0 mL/min with water (5.0 mL), followed by a linear gradient (0-40% v/v) of acetonitrile/water over 40 min. The degree of reduction was determined by integrating the newly formed peak in the chromatogram corresponding to reduced βME (elution time of 6 min) at 205 nm. Calibration curves were generated and determined to be linear over the concentration range. The amount of residual oxidized BME was calculated, and the second-order rate constants were determined from the linear fit of the data in FIG. 1A ($k_{obs}= [(1/C_{final})-(1/C_{initial})]/t$). The initial values of concentration ($C_{initial}$) were: BMMP, DMH, DTBA, or DTT=$\beta ME^{ox}$=5 mM. Values of $k_{obs}$ (Table 2) are the mean±SE from three independent experiments. The same procedure was repeated with BMMP, DTBA, and DTT in 50 mM sodium acetate buffer, pH 5.0.

Reactivation of Papain

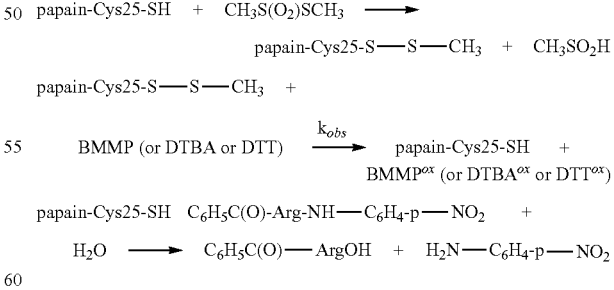

Papain was inactivated by forming a mixed disulfide upon treatment of its active-site cysteine (Cys25) with S-methyl methanethiosulfonate following a procedure reported previously. [31, 23] A 1.25 mL solution of papain-Cys25-S—S—$CH_3$ ($4.4\times10^{-6}$ M) in a degassed 0.10 M imidazole-HCl buffer, pH 7.0, containing EDTA (2 mM) was placed in a 1.5-mL LoBind Eppendorf tube. At time t=0, 10 μL of a 1 mM stock solution of BMMP was added, and a timer was started. The initial concentrations of the reaction mixture were dithiol reducing agent: $7.9 \times 10^{-6}$ M and inactive protein: $4.4 \times 10^{-6}$ M. At various time points, a 200-μL aliquot of the reaction mixture was removed and added to a cuvette containing 800 μL of substrate solution (0.10 M imidazole-HCl buffer, pH 6.0, containing 2 mM EDTA and 1.25 mM N-benzoyl-L-arginyl-p-nitroanilide), and the rate of change in absorbance at 410 nm was recorded at 25° C. A unit of protein is defined as the amount of enzyme required to produce 4-nitroaniline at a rate of 1 μmol/min. The units of active papain at each time point were calculated by using an extinction coefficient for 4-nitroaniline of $\epsilon = 8,800$ $M^{-1}cm^{-1}$ at 410 nm. In order to determine the possible number of units of active papain in the reaction mixture, enzymatic activity was assessed after a large excess of DTT (~100 fold) was added to an Eppendorf tube. As a control, the addition of DTT was shown to have no bearing on the assay data, other than in activating the enzyme. Y=enzymatic activity (%) at any time point was determined by dividing the number of active units of enzyme by the possible number of units in the solution, and plotted in FIG. 2A. To determine the value of the second-order rate constant ($k_{obs}$) for the reducing agents, the second order rate equation (eq 4) was transformed into eq 5, which was fitted to the data with the program Prism 5.0. In both equations, $A_0$=[inactive protein]$_{t=0}$, A=[inactive protein]$_t$=$A_0$−$A_0$Y, $B_0$=[reducing agent]$_{t=0}$, and B=[reducing agent]$_t$=$B_0$−$A_0$Y. Values of $k_{obs}$ were the mean±SE from three separate experiments: BMMP, $k_{obs}$=(1139±62) $M^{-1}s^{-1}$; DTBA, $k_{obs}$=(950±51) $M^{-1}s^{-1}$; and DTT, $k_{obs}$=(87±3) $M^{-1}s^{-1}$.

$$\frac{1}{B_o - A_o} \ln \frac{A_o B}{A B_o} = k_{obs} t \quad (4)$$

$$y = \frac{B_o - B_o e^{k_{obs} t(A_o - B_o)}}{B_o - A_o e^{k_{obs} t(A_o - B_o)}} \quad (5)$$

Reactivation of Creatine Kinase

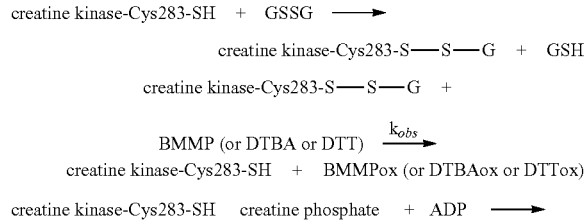

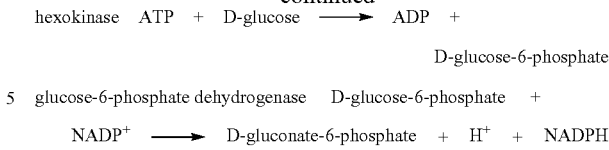

The oxidation and subsequent reactivation of creatine kinase with BMMP (or DTBA or DTT) was accomplished by a procedure described previously. [21, 23] Enzymatic activity (%) at particular time points was calculated by dividing the number of active units of enzyme by the possible number of units in solution, and was plotted in FIG. 2B. Values of $k_{obs}$ (Table 2) were determined using eq. 5 as described above, and were the mean±SE for three separate experiments: BMMP, $k_{obs}$=(476±34) $M^{-1}s^{-1}$; DTBA, $k_{obs}$=(70±2) $M^{-1}s^{-1}$; and DTT, $k_{obs}$=(82±3) $M^{-1}s^{-1}$.

TABLE 2

Values of $K_{obs}$ ($M^{-1}s^{-1}$) for the reduction of disulfides by dithiols

| Disulfide | BMMP | DMH | DTBA | DTT |
|---|---|---|---|---|
| βME$^{ox}$, pH 7.0 | 1.02 ± 0.07 | 0.56 ± 0.04 | 0.32 ± 0.02 | 0.090 ± 0.005 |
| βME$^{ox}$, pH 5.0 | 0.0183 ± 0.0007 | ND$^a$ | 0.0051 ± 0.0004 | 0.0013 ± 0.0001 |
| papain-Cys25-S-S-CH$_3$ | 1139 ± 62 | ND$^a$ | 950 ± 51 | 87 ± 3 |
| creatine kinase-Cys283-S-S-G | 476 ± 34 | ND$^a$ | 70 ± 2 | 82 ± 3 |

$^a$ND, not determined.

Determination of BMMP Solubility in Buffered Water

A 20 mM stock solution of 2-butyne-1,4-diol (an $^1$H NMR standard) was prepared in 50 mM sodium phosphate buffer, pH 7.0. BMMP was added to a solution containing 1 mL of this buffer and 0.1 mL of D$_2$O until the solution was saturated completely. The mixture was sonicated to ensure complete dissolution and filtered into an NMR tube, and its spectrum was acquired. The solubility of BMMP was determined to be (64±14) mM by integration of the $^1$H NMR peak areas of the aryl CH and methylene CH$_2$SH protons for BMMP and the CH$_2$OH peak for 2-butyne-1,4-diol.

REFERENCES

1. P. C. Jocelyn, ed., Biochemistry of the SH Group: The Occurrence, Chemical Properties, Metabolism and Biological Function of Thiols and Disulfides, London, U.K., 1972.
2. C. Jacob, G. I. Giles, N. M. Giles and H. Sies, Angew. Chem. Int. Ed., 2003, 42, 4742-4758.
3. J. Buchner and L. Moroder, eds., Oxidative Folding of Peptides and Proteins, The Royal Society of Chemistry, Cambridge, UK, 2009.
4. M. Lindahl, A. Mata-Cabana and T. Kieselbach, Antioxid. Redox Signal., 2011, 14, 2581-2642.
5. H. F. Gilbert, Adv. Enzymol., 1990, 63, 69-172.
6. P. S. Kim and R. L. Baldwin, Annu. Rev. Biochem., 1990, 59, 631-660.
7. W. W. Cleland, Biochemistry, 1964, 3, 480-482.
8. R. P. Szajewski and G. M. Whitesides, J. Am. Chem. Soc., 1980, 102, 2011-2026.
9. G. V. Lamoureux and G. M. Whitesides, J. Org. Chem., 1993, 58, 633-641.
10. K. Van Laer, C. J. Hamilton and J. Messens, Antioxid. Redox Signal., 2013, 18, 1642-1653.

11. G. M. Whitesides, J. E. Lilburn and R. P. Szajewski, J. Org. Chem., 1977, 42, 332-338.
12. J. P. Snyder and L. Carlsen, J. Am. Chem. Soc., 1977, 99, 2931-2942.
13. R. E. Rosenfield, R. Parthasarathy and J. D. Dunitz, J. Am. Chem. Soc., 1977, 99, 4860-4862.
14. Z. Shaked, R. P. Szajewski and G. M. Whitesides, Biochemistry, 1980, 19, 4156-4166.
15. J. Houk and G. M. Whitesides, J. Am. Chem. Soc., 1987, 109, 6825-6836.
16. D. A. Keire, E. Strauss, W. Guo, B. Noszal and D. L. Rabenstein, J. Org. Chem., 1992, 57, 123-127.
17. D. M. Rothwarf and H. A. Scheraga, Proc. Natl. Acad. Sci. U.S.A., 1992, 89, 7944-7948.
18. P. A. Fernandes and M. J. Ramos, Chem. Eur. J., 2004, 10, 257-266.
19. W. J. Lees and G. H. Whitesides, J. Org. Chem., 1993, 58, 642-647.
20. R. A. Bednar, Biochemistry, 1990, 29, 3684-3690.
21. R. Singh and G. M. Whitesides, J. Org. Chem., 1991, 56, 2332-2337.
22. W. J. Lees, R. Singh and G. M. Whitesides, J. Org. Chem., 1991, 56, 7328-7331.
23. J. C. Lukesh, III, M. J. Palte and R. T. Raines, J. Am. Chem. Soc., 2012, 134, 4057-4059.
24. J. C. Lukesh, III, B. Vanveller and R. T. Raines, Angew. Chem. Int. Ed., 2013, 52, 12901-12904.
25. J. A. Burns and G. M. Whitesides, J. Am. Chem. Soc., 1990, 112, 6296-6303.
26. W. P. Jencks, in Catalysis in Chemistry and Enzymology, McrGraw-Hill, New York, N.Y., 1969, pp. 79-85.
27. R. E. Benesch and R. J. Benesch, J. Am. Chem. Soc., 1955, 77, 5877-5881.
28. A. S. Patel and W. J. Lees, Bioorg. Med. Chem., 2012, 20, 1020-1028.
29. K. K. Millis, K. H. Weaver and D. L. Rabenstein, J. Org. Chem., 1993, 58, 4144-4146
30. I. Schechter and A. Berger, Biochem. Biophys. Res. Commun., 1967, 27, 157-162.
31. D. J. Smith, E. T. Maggio and G. L. Kenyon, Biochemistry, 1975, 14, 766-771.
32. S. Putney, W. Herlihy, N. Royal, H. Pang, H. V. Aposhian, L. Pickering, R. Belagaje, K. Biemann, D. Page, S. Kuby and P. Schimmel, J. Biol. Chem., 1984, 259, 4317-4320.
33. L. H. Chen, C. L. Borders, J. R. Vasquez and G. L. Kenyon, Biochemistry, 1996, 35, 7895-7902.
34. J. K. M. Rao, G. Bujacz and A. Wlodawer, FEBS Lett., 1998, 439, 133-137.
35. A. M. Hurne, C. L. L. Chai and P. Waring, J. Biol. Chem., 2000, 275, 25202-25206.
36. D. A. Keyworth, J. Org. Chem., 1959, 24, 1355.
37. J. H. Liu, A. T. Wu, M. H. Huang, C. W. Wu and W. S. Chung, J. Org. Chem., 2000, 65, 3395-3403.
38. K. J. Woycechowsky, K. D. Wittrup and R. T. Raines, Chem. Biol., 1999, 6, 871-879.
39. Peyrottes, S., Egron, D., Lefebvre, I., Gosselin, G., Imbach J.-L. and C. Perigaud (2004) SATE Pronucleotide Approaches: An Overview Mini-Reviews in Medicinal Chemistry 4:395-408.
40. Perigaud, C.; Gosselin, G.; Imbach, J.-L. In Current Topics in Medicinal Chemistry; Alexander, J. C. Ed.; Blackwell Science Ltd: Oxford, 1997; Vol. 2, pp 15-29.
41. Peyrottes, S., and Perigaud, C. (2007) Chemistry of bis-SATE Mononucleotide Prodrugs Current Protocols in Nucleic Acid Chemistry (Supplment 29) unit 15.3 15.3.1-15.3.13.
42. Oetke, C. et al. (2002) Versatile Biosynthetic Engineering of Sialic Acid in Living Cells Using Synthetic Sialic Acid Analogues J. Biol. Chem. 277:6688-6695.
43. Lee C-H., Huang, H—C and Juan, H-F (2011)Re Int. J. Mol. Sci. 2011, 12, 5304-5318
44. Cumming, R. C. et al. (2004) Protein Disulfide Bond Formation in the Cytoplasm during Oxidative Stress J. Biol. Chem, 279:21749-21758.
45. McCord, J. M. (1994) Science 266(5190):1586-1587.
46. Furukawa, Y. et al. (2006) Proc. Nat'l Acad. Sci. USA 103(18):7148-7153.

We claim:

1. A compound of formula I or formula II:

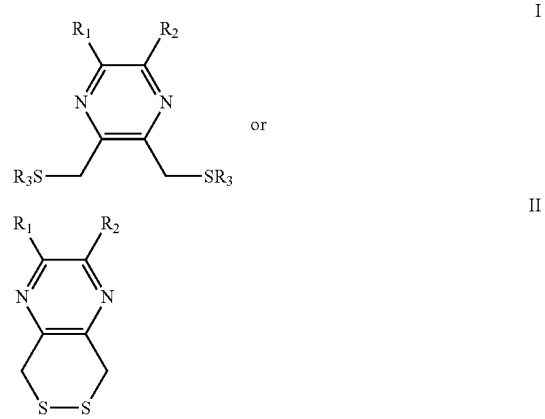

or salts thereof, wherein:

$R_1$ and $R_2$, independently, are hydrogen, halogen, —CN, optionally substituted alkyl, -alkoxyalkyl, —CO—$R_6$, —CO—O$R_6$, —O—CO—$R_6$, —CO—$CH_2$—CO—O—$R_6$, —NH—CO—$R_6$, —CO—N($R_6$)$_2$, —NH—CO—N($R_6$)$_2$, a divalent linker carrying a reactive group, a divalent linker immobilized to a surface, or a divalent linker conjugated to a biological or chemical species, where each $R_6$ independently is hydrogen, an alkyl group having 1-6 carbon atoms or an alkoxyalkyl group;

each $R_3$ is independently hydrogen or a —CO$R_7$ group, where $R_7$ is independently hydrogen, an alkyl group, an alkylalkoxy group, an aryl group, a heterocyclyl group, or a heteroaryl group, wherein each alkyl, alkylalkoxy, aryl, heterocyclyl or heteroaryl group is optionally substituted with one or more non-hydrogen substituents; and optional substituents are selected from one or more —OH, halogen, —CN, —$N_3$, —$NO_2$, —OCN, —NCO, —SCN, —NCS, alkyl, haloalkyl, alkoxy, alkoxyalkyl, haloalkoxy, —$NH_2$, —CO—O$R_8$, —O—CO—$R_8$, —CO—$R_8$, —CO—$CH_2$—$CO_2$—$R_8$, —NH—CO—$R_8$, —CO—N($R_8$)$_2$, —N($R_8$)$_2$, or —NH—CO—N($R_8$)$_2$, where each $R_8$ independently is hydrogen, an alkyl group having 1-6 carbon atoms or an alkoxyalkyl group, wherein:

the surface is glass, silica, silica gel, metal oxide, gold, magnetic material, paramagnetic material, supermagnetic material, plastic, resin, or polymer;

the reactive group is selected from the group consisting of an acid chloride group, an acyl azide group, an acetamidyl group, an acryloyl group, an aldehyde group, an alkenyl group, an alkynyl group, an amino group, an amide group, an anhydride group, an azide group, a carbohydrazide group, a carboxyl group, a carboxylate group, a diazoalkyl group, a diazoaryl group, a diazoacetyl group, a 2,2'-dihydroxy-6,6'-dinaphthyldisulfide group, a dithiopyridyl group, an N,N'-disuccinimidyl carbonate group, an epoxide group, a haloacetyl group, a haloacetamidyl group, a haloalkyl group, a halobenzyl group, a hydroxyl group, a N-hydroxysuccinimidyl chloroformate group, a hydrazine group, a hydrazide group, a hydroxyl group, an imidoester group, an isothiocyanate group, an isocyanate group, a ketone group, a maleimide group, a phosphinothioester group, a semicarbazide group, a sulfhydryl group, a sulfamyl group, a sulfonylhydrazide group, a thiosulfate group, and an active ester group which is selected from a tosylester, a mesylester, a tresylester, a succinimidyl ester, sulfosuccinimidyl ester, a haloalkyl ester group, a halophenyl ester group, a nitrophenyl ester group, and a sulfodichlorophenol ester group;

the biological or chemical species is selected from a peptide, a protein, a carbohydrate, a nucleic acid, a fluorescent label, a radio label, an isotopic label, a ligand which binds to a peptide or protein, an enzyme substrate and a pharmacophore, and the divalent linker is selected from:

an alkylene, wherein one or more carbons are optionally substituted with one or more substituents selected from halogen, hydroxyl, and alkyl groups having 1-3 carbon atoms;

a cycloalkylene having a 3-8 member ring wherein one or more carbons are optionally substituted with one or more substituents selected from halogen, hydroxyl and alkyl groups having 1-3 carbon atoms;

an alkenylene containing one or more double bonds, wherein one or more carbons are optionally substituted with one or more substituents selected from halogen, hydroxyl and alkyl groups having 1-3 carbon atoms;

an alkoxyalkylene, a phenylene wherein one to four of the ring carbons are optionally substituted with one or more substituents selected from halogen, a nitro group, a cyano group, hydroxyl, and alkyl groups having 1-3 carbon atoms;

a naphthylene, wherein one to eight of the ring carbons are optionally substituted with one or more substituents selected from halogen, a nitro group, a cyano group, hydroxyl, and an alkyl group having 1-3 carbon atoms;

a biphenylene, wherein one to eight of the ring carbons are optionally substituted with one or more substituents selected from halogen, hydroxyl, and an alkyl group having 1-3 carbon atoms;

a heterocyclylene having a 3-8-member ring with 1-3 heteroatoms, selected from N, O and S, wherein one or more carbons or heteroatoms of the heterocyclylene are optionally substituted with one or more substituents selected from halogen, a nitro group, hydroxyl, and an alkyl group having 1-3 carbon atoms;

a heteroarylene having a 5- or 6-member heteroaryl ring having 1-3 heteroatoms selected from N, O and S, wherein one or more carbons or heteroatoms of the heteroarylene are optionally substituted with one or more substituents selected from halogen, a nitro group, hydroxyl, or an alkyl group having 1-3 carbon atoms; and —R-[L]$_a$-R'— or —R-[L]$_a$-, where:

—R— and —R'— are independently selected from:

—O—, —S—, —NR$_c$—, —CO—, —O—CO—, —CO—O—, —OCOO—, —CO—NR$_c$—, —NR$_c$—CO—, —NR$_c$—CO—NR$_c$—, —OCO—NR$_c$—, —NR$_c$—CO—O—, —N=N—, —N=N—NR$_c$—, —CO—S—, —S—CO—, —SO$_2$—, —SO$_2$—NR$_c$, —SO$_2$—NR$_c$—CO—, —NR$_c$—CS—NR$_c$—, or —CR$_c$(OH)—CR$_c$(OH)—, where R$_c$ is hydrogen or an alkyl group having 1-3 carbon atoms; and L is a spacer group, where a is 0 or 1, and the spacer is selected from an alkylene, a cycloalkylene, an alkenylene, an alkoxyalkylene, a phenylene, a naphthylene, a biphenylene, a heterocyclylene, or a heteroarylene.

2. The compound of claim 1 wherein at least one of R$_1$ or R$_2$ is an alkoxyalkyl group.

3. The compound of claim 1 wherein at least one of R$_1$ or R$_2$ is a —R-[L]$_a$-R'-T group, where —R-[L]$_a$-R'— is a divalent linker, and where:

—R— and —R'— are independently selected from —O—, —S—, —NR$_c$—, —CO—, —O—CO—, —CO—O—, —OCOO—, —CO—NR$_c$—, —NR$_c$—CO—, —NR$_c$—CO—NR$_c$—, —OCO—NR$_c$—, —NR$_c$—CO—O—, —N=N—, —N=N—NR$_c$—, —CO—S—, —S—CO—, —SO$_2$—, —SO$_2$—NR$_c$, —SO$_2$—NR$_c$—CO—, —NR$_c$—CS—NR$_c$—, or —CR$_c$(OH)—CR$_c$(OH)—, where R$_c$ is hydrogen or an alkyl group having 1-3 carbon atoms;

L is a spacer group, where a is 0 or 1, and the spacer is selected from an alkylene, a cycloalkylene, an alkenylene, an alkoxyalkylene, a phenylene, a naphthylene, a biphenylene, a heterocyclylene, or a heteroarylene; and T represents the surface or the biological or chemical species.

4. The compound of claim 1 wherein at least one of R$_1$ or R$_2$ is a —R-[L]$_a$-R$_L$ group where:

—R$_L$ represents the reactive group;

—R— is selected from —O—, —S—, —NR$_c$—, —CO—, —O—CO—, —CO—O—, —OCOO—, —CO—NR$_c$—, —NR$_c$—CO—, —NR$_c$—CO—NR$_c$—, —OCO—NR$_c$—, —NR$_c$—CO—O—, —N=N—, —N=N—NR$_c$—, —CO—S—, —S—CO—, —SO$_2$—, —SO$_2$—NR$_c$, —SO$_2$—NR$_c$—CO—, —NR$_c$—CS—NR$_c$—, or —CR$_c$(OH)—CR$_c$(OH)—, where R$_c$ is hydrogen or an alkyl group having 1-3 carbon atoms; and L is a spacer group, where a is 0 or 1, and the spacer is selected from an alkylene, a cycloalkylene, an alkenylene, an alkoxyalkylene, a phenylene, a naphthylene, a biphenylene, a heterocyclylene, or a heteroarylene.

5. The compound of claim 1 of formula I.

6. The compound of claim 1 wherein R$_3$ is hydrogen or an acyl group.

7. The compound of claim 1 of formula II.

8. The compound of claim 1 which is immobilized on the surface.

9. The compound of claim 1 which is conjugated to the biological or chemical species.

10. A kit comprising one or more compounds of claim 1 in combination with one or more components selected from one or more molecules having one or more sulfhydryl groups, or one or more solvents or buffers.

11. A method for reducing or preventing disulfide bond formation in one or more molecules having one or more sulfhydryl groups which comprises the step of contacting the one or more molecules having one or more sulfhydryl groups with one or more compounds of formula I of claim 1.

12. The method of claim 11 wherein the one or more compounds are covalently immobilized to the surface.

13. The method of claim 11 wherein the molecules having one or more sulfhydryl groups are peptides or proteins.

14. A compound of formula I or formula II:

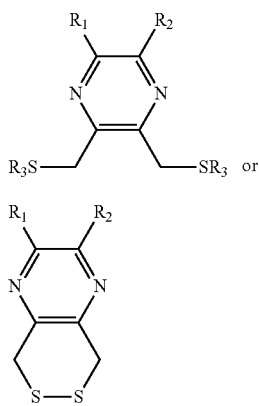

I

II or salts thereof, wherein:

$R_1$ and $R_2$, independently, are hydrogen, halogen, —CN, optionally substituted alkyl, -alkoxyalkyl, —CO—$R_6$, —CO—O$R_6$, —O—CO—$R_6$, —CO—CH$_2$—CO—O—$R_6$, —NH—CO—$R_6$, —CO—N($R_6$)$_2$, or —NH—CO—N($R_6$)$_2$, where each $R_6$ independently is hydrogen, an alkyl group having 1-6 carbon atoms or an alkoxyalkyl group;

$R_3$ is independently hydrogen or a —CO$R_S$ group, where $R_7$ is independently hydrogen, an alkyl group, an alkylalkoxy group, an aryl group, a heterocyclyl group, or a heteroaryl group, wherein each alkyl, alkylalkoxy, aryl, heterocyclyl or heteroaryl group is optionally substituted with one or more non-hydrogen substituents; and optional substituents are one or more —OH, halogen, —CN, —N$_3$, —NO$_2$, —OCN, —NCO, —SCN, —NCS, alkyl, haloalkyl, alkoxy, alkoxyalkyl, haloalkoxy, —NH$_2$, —CO—O$R_8$, —O—CO—$R_8$, —CO—$R_8$, —CO—CH$_2$—OO$_2$—$R_8$, —NH—CO—$R_8$, —CO—N($R_8$)$_2$, —N($R_8$)$_2$, or —NH—CO—N($R_8$)$_2$, where each $R_8$ independently is hydrogen, an alkyl group having 1-6 carbon atoms or an alkoxyalkyl group.

15. The compound of claim 14 of formula I or a salt thereof.

16. The compound of claim 15, wherein:

$R_1$ and $R_2$, independently, are hydrogen, optionally substituted alkyl, -alkoxyalkyl, —CO—$R_6$, —NH—CO—$R_6$, —CO—N($R_6$)$_2$, or —NH—CO—N($R_6$)$_2$, where each $R_6$ independently is hydrogen, an alkyl group having 1-6 carbon atoms or an alkoxyalkyl group.

17. The compound of claim 14 having formula I, wherein both of $R_1$ and $R_2$ are hydrogen and $R_3$ is independently hydrogen or a —CO$R_7$ group, where $R_7$ is hydrogen or an alkyl group having 1-3 carbon atoms.

18. The compound of claim 14 having formula I, wherein $R_1$, $R_2$ and both $R_3$ are hydrogen.

19. The compound of claim 14 wherein $R_3$ is hydrogen or an acyl group.

20. The compound of claim 14 of formula II or a salt thereof.

21. The compound of claim 14 having formula II, wherein $R_1$, and $R_2$ are hydrogen.

* * * * *